United States Patent
Shi et al.

(10) Patent No.: US 6,657,224 B2
(45) Date of Patent: Dec. 2, 2003

(54) ORGANIC LIGHT EMITTING DIODE DEVICES USING THERMOSTABLE HOLE-INJECTION AND HOLE-TRANSPORT COMPOUNDS

(75) Inventors: Xiaobo Shi, Poughquag, NY (US); Igor Sokolik, Verbank, NY (US)

(73) Assignee: eMagin Corporation, Hopewell Junction, NY (US)

( * ) Notice: Subject to any disclaimer, the term of this patent is extended or adjusted under 35 U.S.C. 154(b) by 0 days.

(21) Appl. No.: 09/894,502

(22) Filed: Jun. 28, 2001

(65) Prior Publication Data
US 2003/0030059 A1 Feb. 13, 2003

(51) Int. Cl.[7] .............................................. H01C 27/15
(52) U.S. Cl. ......................................... 257/40; 257/79
(58) Field of Search ........................ 257/40, E51.001, 257/E51.018, E51.002, E51.024, E51.26, 79, 103

(56) References Cited

U.S. PATENT DOCUMENTS

| 5,536,949 A | * 7/1996 | Hosokawa et al. ........... 257/40 |
| 6,114,055 A | * 9/2000 | Choong et al. ............. 428/690 |
| 6,194,089 B1 | * 2/2001 | Choong et al. ............. 428/690 |
| 6,406,804 B1 | * 6/2002 | Higashi et al. ............. 428/690 |
| 2002/0034655 A1 | * 3/2002 | Watanabe et al. ........... 428/690 |

FOREIGN PATENT DOCUMENTS

| EP | 0848 579 | 12/1997 | ........... H05B/33/14 |
| EP | 0 969 532 | 6/1999 | ........... H01L/51/20 |
| EP | 0 973 210 | 7/1999 | ........... H01L/51/20 |
| JP | 04320485 A | * 11/1992 | ........... C09K/11/00 |
| WO | WO 99/20596 | 10/1998 | ........ C07C/211/54 |

* cited by examiner

*Primary Examiner*—Eddie Lee
*Assistant Examiner*—Paul E Brock, II
(74) *Attorney, Agent, or Firm*—Bazerman & Drangel, PC

(57) ABSTRACT

The present invention relates to multi-layered organic light emitting diode devices having hole-injection and/or hole-transport layers comprising aryl amine compounds with relatively high glass transition temperatures (i.e., thermostable aryl amine compounds). Such multi-layered OLED devices allow for a staircase change in the energy difference of holes and electrons as they migrate from the electrodes toward the emitter layer, resulting in a lower operating voltage and a high quantum yield of luminescence for a given current density. The present invention also relates to microdisplay devices comprising multi-layered organic light emitting diode devices having hole-injection and/or hole-transport layers comprising thermostable aryl amine compounds.

79 Claims, 2 Drawing Sheets

ORGANIC LIGHT EMITTING DIODE DEVICES USING THERMOSTABLE HOLE-INJECTION AND HOLE-TRANSPORT COMPOUNDS

STATEMENT REGARDING FEDERALLY SPONSORED RESEARCH OR DEVELOPMENT

This research was sponsored by U.S. Government contract DUAP contract number F33615-98-2-5156.

CROSS-REFERENCE TO RELATED APPLICATIONS

Not applicable.

BACKGROUND OF THE INVENTION

Organic electroluminescent devices also known as organic light emitting diode ("OLED") devices comprise an anode, a cathode and an electroluminescent medium made up of extremely thin layers (typically less than 1.0 micrometer in combined thickness) separating the anode and the cathode. A basic two-layer light emitting diode comprises one organic layer that is specifically chosen to inject and transport holes and a second organic layer that is specifically chosen to inject and transport electrons. The interface between the two layers provides an efficient site for the recombination of the injected hole-electron pair, which results in electroluminescence. The electroluminescent medium can comprise additional layers, including, but not limited to, an emitter layer between the hole injection and transport and the electron injection and transport layers in which recombination of holes and electrons occurs. Since light emission is directly related to current density through the organic electroluminescent medium, the thin layers coupled with increased charge injection and transport efficiencies have allowed acceptable light emission levels (e.g., brightness levels capable of being visually detected in ambient light) to be achieved with low applied voltages in ranges compatible with integrated circuit drivers, such as field effect transistors.

A large variety of organic compounds having the appropriate characteristics can be used in the layers of the electroluminescent medium. For example, variations in the chemical structures of compounds in the various layers can result in changes in ionization potential, mobility of holes or electrons, or the wavelength of emitted light. Nevertheless, the performance of OLEDs may be limited by the organic materials, rendering them undesirable for many applications.

Hole-injection and hole-transport organic compounds have tended to be an unstable part of the electroluminescent medium of OLEDs. These materials are thought to undergo a morphological change when exposed to increased temperatures or when stored for long periods of time. Since efficient operation of the hole-injection and hole-transport layers depends on their amorphous nature, morphological changes may lead to degradation of the OLED. The temperature at which morphological changes occur and an amorphous material becomes crystalline is the glass transition temperature of the material. The glass transition temperature of hole-injection and hole-transport compounds has generally been below 100° C.

Triarylamine derivatives such as N,N'-diphenyl-N,N'-bis (3-methylphenyl)-1,1'-biphenyl-4,4'-diamine (TPD) and N,N'-bis(1-naphthyl)-N,N'-diphenyl-1,1'-biphenyl-4,4'-diamine (NPD) are the most widely used derivatives in the hole injection and hole transport layers of OLEDs (Tang et al. (1987) *Appl. Phys. Let.* 51:913–15; Mitschke et al. (2000) *J. Mater. Chem.* 10:1471–1507). However, these triarylamines tend to crystallize on aging or if left at ambient temperatures. Improvements to the stability of hole-injection and hole-transport materials have been made, including inserting a triarylamine derivative into a polymer matrix or covalently attaching triarylamines to a polymer backbone (Mitschke et al. (2000)). In addition, hole-transport and hole-injection materials, such as the "starburst amines," have been designed that have higher glass transition temperatures (Kurwabara et al. (1994) *Adv. Mater.* 6:677; JP 07997305 to Shirota et al; EP 00508562 A1 to Shirota et al.; JP 09012548 to Shirota et al.; JP 08291115 to Shirota et al.; and JP 06312979 to Shirota et al).

Discussion or citation of a reference herein shall not be construed as an admission that such reference is prior art to the present invention.

BRIEF SUMMARY OF THE INVENTION

In a first embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1:

(1)

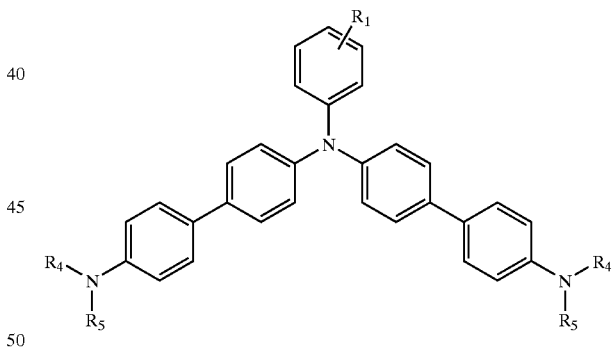

wherein $R_1$ is selected from the group consisting of biphenyl, naphthyl, phenyl and

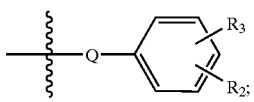

Q is selected from the group consisting of a bond, $C_1$–$C_4$ alkyl, —C(O)—, —S(O)—, —O—Si—O—, —O—Ge—O—, —O—,

and

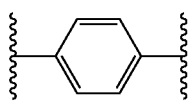

R$_2$ and R$_3$ are each independently selected from the group consisting of aryl, F, Cl, —CF$_3$, saturated alkyl of up to 10 carbon atoms, SO$_2$R$_6$, Si(R$_6$)$_3$, and OR$_6$, or R$_2$ and R$_3$ taken together form a heterocyclic ring of up to 8 atoms, wherein one of the 8 atoms is nitrogen and another of the 8 atoms is either nitrogen or oxygen, or R$_2$ and R$_3$ taken together with the phenyl group to which they are attached form a fused polycyclic aromatic system, wherein the fused polycyclic aromatic system comprises up to 16 carbon atoms;

R$_4$ and R$_5$ are each independently selected from the group consisting of:

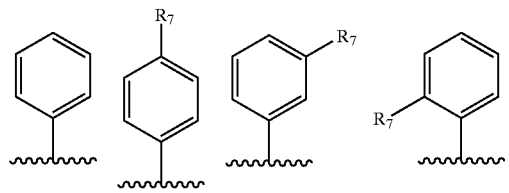

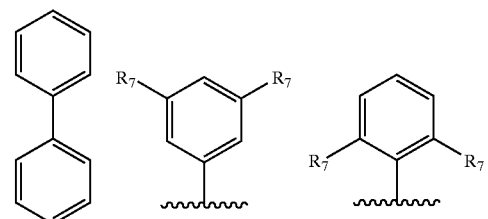

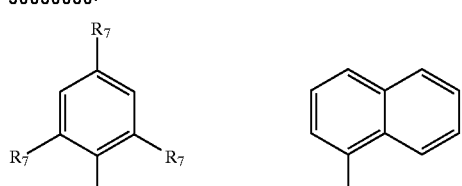

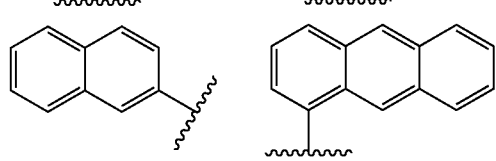

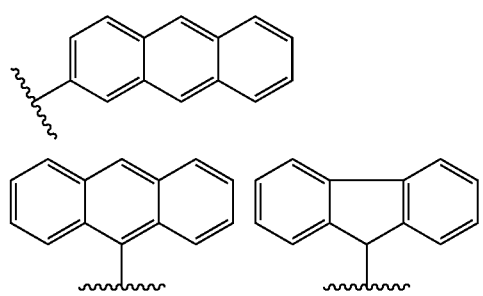

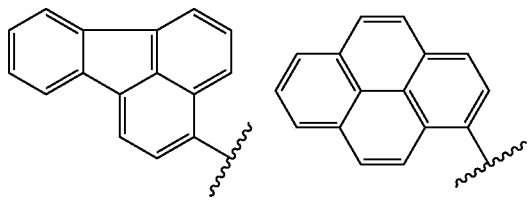

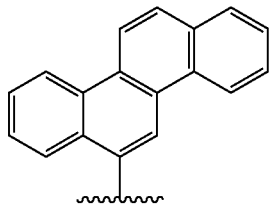

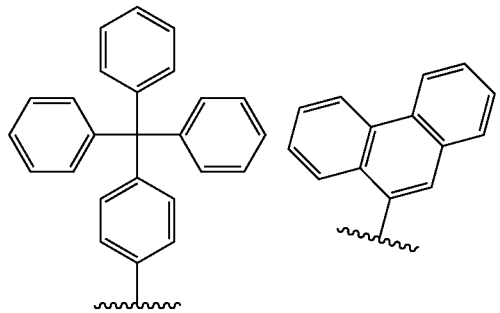

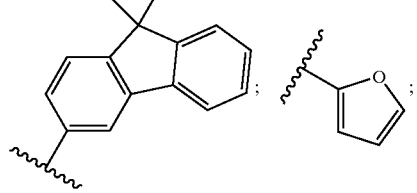

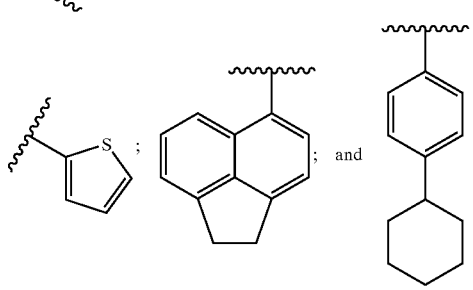

or R$_4$ and R$_5$ taken together with the nitrogen to which they are attached are selected from the group consisting of:

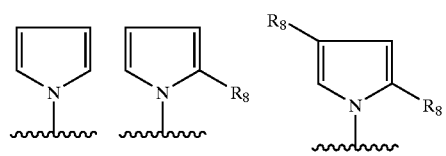

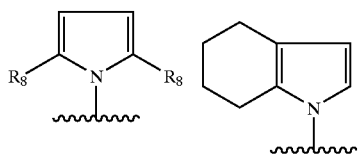

-continued

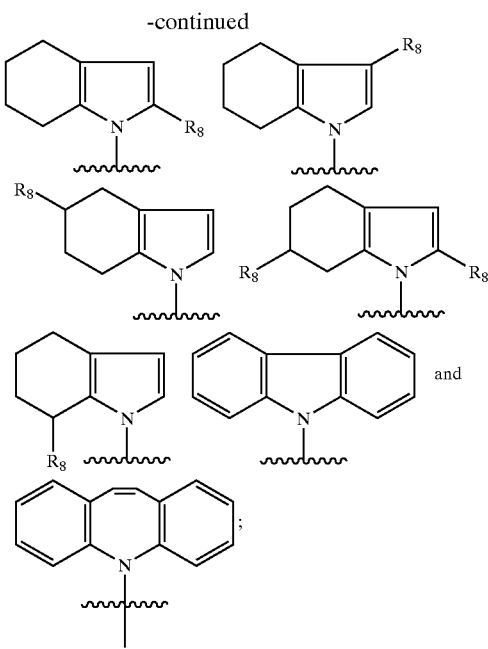

$R_6$ is $C_1$–$C_4$ straight or branched saturated alkyl;

$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$;

$R_9$ is selected from the group consisting Of $C_1$–$C_6$ alkyl and aryl; and wherein one of the bottom electrode and the top electrode is a cathode and the other is an anode.

In a second embodiment, the present invention relates to an organic light emitting diode device comprising: (a) a cathode; (b) an anode; (c) a layer formed from at least one electron-injection/electron-transport material that is adjacent to the cathode; (d) a hole-injection layer that is adjacent to the anode; and (e) at least one hole-transport layer that is adjacent to the hole-injection layer, wherein at least one of the hole-injection and hole-transport layers comprises a compound of formula 1, wherein one of the bottom electrode and the top electrode is a cathode and the other is an anode.

In a third embodiment, the present invention relates to an organic light-emitting diode device that emits green light, comprising: (a) a bottom electrode that is an anode comprising indium tin oxide; (b) a hole-injection layer adjacent to the anode comprising bis(N,N'-1-naphthyl-phenyl-amino-biphenyl)-biphenyl amine (BPA-DNPB); (c) a hole-transport layer adjacent to the hole-injection layer comprising bis(carbazol-N-biphenyl)-biphenyl amine (BPA-BCA); (d) an emitter layer adjacent to the hole-transport layer comprising tris(hydroxyquinoline) aluminum (ALQ) and a compound selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, and mixtures thereof; (e) an electron-transport layer adjacent to the emitter layer comprising ALQ; and (f) a top electrode that is a cathode comprising lithium fluoride and aluminum or magnesium and silver.

In a fourth embodiment, the present invention relates to an organic light-emitting diode device that emits white or blue light, comprising: (a) a bottom electrode that is an anode comprising indium tin oxide; (b) a hole-injection layer adjacent to the anode comprising BPA-DNPB; (c) a hole-transport layer adjacent to the hole-injection layer comprising BPA-BCA; (d) an emitter layer adjacent to the hole-transport layer comprising DCJTB, IDE-120 and IDE-102; (e) an electron-transport layer adjacent to the emitter layer comprising ALQ; and (f) a top electrode that is a cathode comprising lithium fluoride and aluminum.

In a fifth embodiment, the present invention relates to a microdisplay device, comprising: (a) at least one bottom electrode that is an anode; (b) at least one top electrode that is a cathode; and (c) at least two organic layers between the at least one bottom electrode and the at least one top electrode, wherein the at least two organic layers comprise a first organic layer formed from at least one electron-injection/electron-transport material that is adjacent to the at least one cathode and a second organic layer formed from at least one hole-injection/hole-transport material that is adjacent to the at least one anode, the at least one hole-injection/hole-transport material comprising a compound of formula 1.

In a preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_1$ is selected from the group consisting of biphenyl, naphthyl, and phenyl, and wherein one of the bottom electrode and the top electrode is a cathode and the other is an anode.

In another preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_1$ is selected from the group consisting of biphenyl, naphthyl, phenyl and

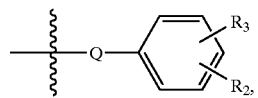

wherein Q is a bond, and wherein one of the bottom electrode and the top electrode is a cathode and the other is an anode.

In yet another preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_2$ and $R_3$ are each aryl, and wherein one of the bottom electrode and the top electrode is a cathode and the other is an anode.

In still another preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_1$ is

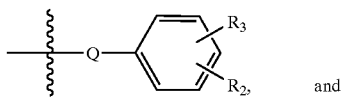

and $R_2$ and $R_3$ are each $C_1$–$C_4$ straight or branched chain alkyl, and wherein one of the bottom electrode and the top electrode is a cathode and the other is an anode.

In another preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_4$ and $R_5$ are taken together with the nitrogen to which they are attached are selected from the group consisting of:

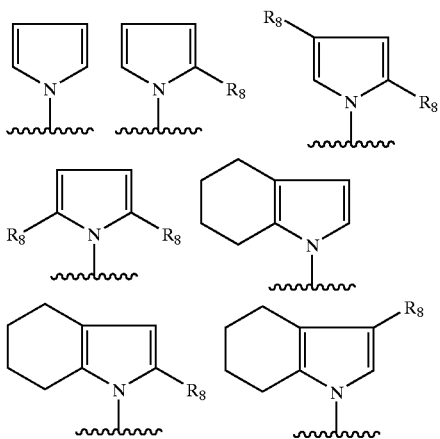

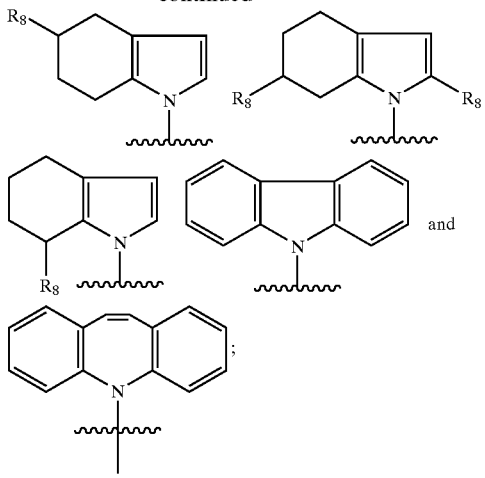

and wherein one of the bottom electrode and the top electrode is a cathode and the other is an anode.

In a more preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_4$ and $R_5$ are taken together with the nitrogen to which they are attached so as to form a heterocycle selected from the group consisting of:

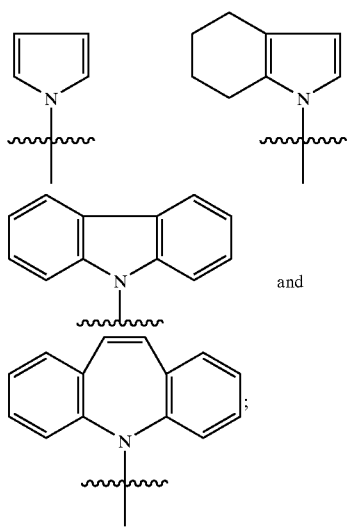

and wherein one of the bottom electrode and the top electrode is a cathode and the other is an anode.

In another preferred embodiment, the present invention relates to an organic light emitting diode device comprising: (a) a cathode; (b) an anode; and (c) at least two organic layers between the anode and the cathode, wherein the at least two organic layers comprise a first organic layer formed from at least one electron-injection/electron-transport material and a second organic layer formed from at least one hole-injection/hole-transport material, wherein the electron-injection/electron-transport material is adjacent to the cathode and the hole-injection/hole-transport material is adjacent to the anode, the at least one hole-injection/hole-transport material comprising a compound of formula 1, wherein $R_4$ and $R_5$ are each independently selected from the group consisting of phenyl, naphthyl, biphenyl, anthracenyl and fluorenyl, and wherein one of the bottom electrode and the top electrode is a cathode and the other is an anode.

DETAILED DESCRIPTION OF THE INVENTION

Fabrication of OLED Devices

OLEDs can be fabricated by any method known to those skilled in the art. In one embodiment, OLEDs are formed by vapor deposition of each layer. In a preferred embodiment, OLEDs are formed by thermal vacuum vapor deposition.

"Bottom electrode," as used herein, means an electrode that is deposited directly onto the substrate.

"Top electrode," as used herein, means an electrode that is deposited at the end of the OLED that is distal to the substrate.

"Hole-injection layer," as used herein, is a layer into which holes are injected from an anode when a voltage is applied across an OLED.

"Hole-transport layer," as used herein, is a layer having high hole mobility and high affinity for holes that is between the anode and the emitter layer. It will be evident to those of skill in the art that the hole-injection layer and the hole-transport layer can be a single layer, or they can be distinct layers comprising different chemical compounds. A compound of formula I is useful both in both hole-injection and hole-transport layers.

"Electron-injection layer," as used herein, is a layer into which electrons are injected from a cathode when a voltage is applied across an OLED.

"Electron-transport layer," as used herein, is a layer having high electron mobility and high affinity for electrons that is between the cathode and the emitter layer. It will be evident to those of skill in the art that the electron-injection layer and the electron-transport layer can be a single layer, or they can be distinct layers comprising different chemical compounds.

Figure 1:
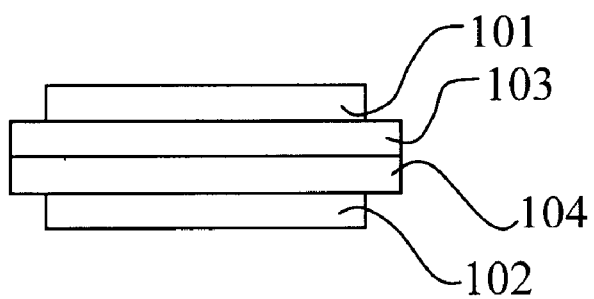
FIG. 1 shows an OLED stack.

In one embodiment, shown in FIG. 1, an OLED comprises a bottom electrode 102, which is either an anode or a cathode, a top electrode 101, which is a cathode if the bottom electrode is an anode and which is an anode if the bottom electrode is a cathode, and an electroluminescent medium having at least two layers 103, 104, one comprising at least one hole-injection/hole-transport material that is adjacent to the anode and the other comprising at least one electron-injection/electron-transport layer that is adjacent to the cathode.

Figure 2:
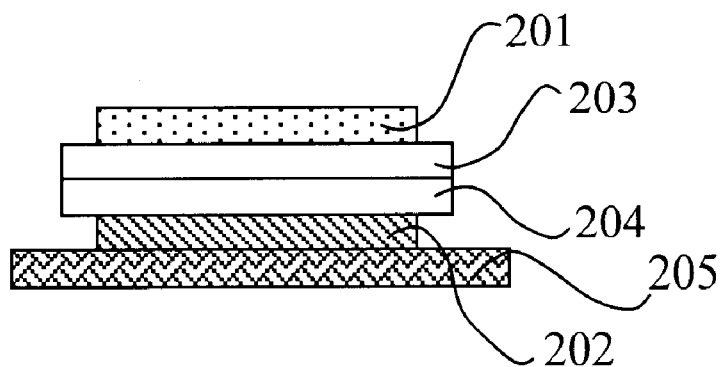
FIG. 2 shows an OLED stack comprising a bottom anode and a top cathode on a substrate.

In another embodiment shown in FIG. 2, the top electrode is the cathode 201 and the bottom electrode, which is deposited directly onto the substrate 205, is the anode 202. Between the cathode and the anode are an electron-injection/electron-transport layer 203 adjacent to the cathode 201 and a hole-injection/hole-transport layer 204 adjacent to the anode 202.

Figure 3:
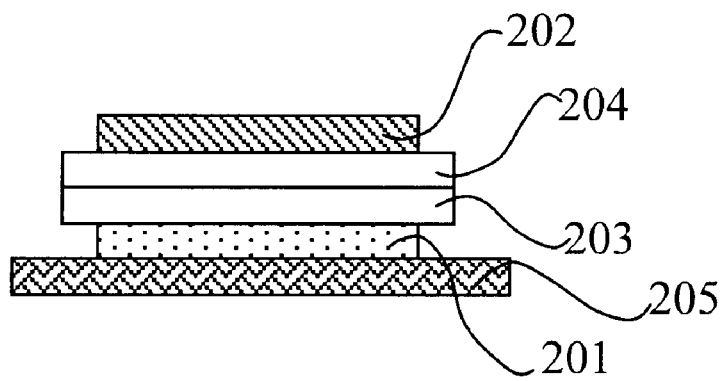
FIG. 3 shows an OLED stack comprising a bottom cathode and a top anode on a substrate.

In another embodiment shown in FIG. 3, the top electrode is the anode 202 and the bottom electrode, which is deposited directly onto the substrate 205, is the cathode 201. Between the cathode and the anode are a hole-injection/hole-transport layer 204 adjacent to the anode 202 and an electron-injection/electron-transport layer 203 adjacent to the cathode 201.

Figure 4:
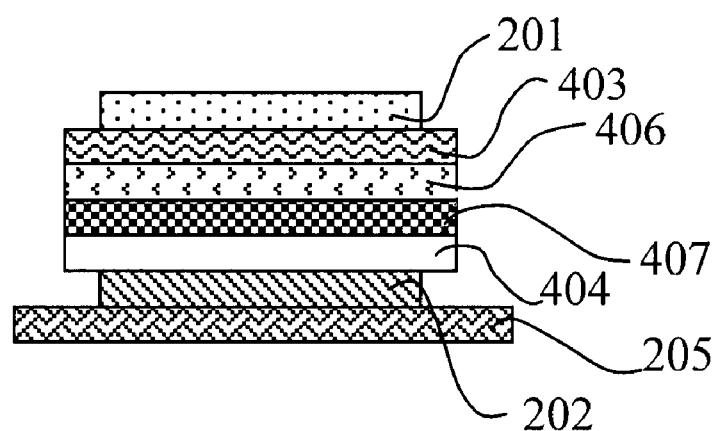
FIG. 4 shows a preferred OLED stack of the present invention.

In yet another embodiment shown in FIG. 4, the top electrode is the cathode 201 and the bottom electrode, which is deposited directly onto the substrate 205, is the anode 202. The OLED further comprises an electron-transport layer 403 adjacent to the cathode 201, a hole-injection/hole-transport layer comprising a hole-injection layer 404 adjacent to the anode 202 and at least one hole-transport layer 407 adjacent to the hole-injection layer 404. Between the electron-transport layer 403 and the hole-transport layer 407, the OLED further comprises an emitter layer 406 wherein holes and electrons recombine to produce light.

In yet another embodiment, the OLED comprises a hole-injection layer adjacent to the anode and at least two hole-transport layers, a first hole-transport layer adjacent to the hole-injection layer and a second hole-transport layer adjacent to the first hole-transport layer.

In one embodiment, the hole-injection layer and the at least two hole-transport layers are deposited separately. In another embodiment, at least two of the layers are inter-deposited.

In other embodiments, the OLED comprises an electron-injection layer and at least one electron-transport layer.

In yet another embodiment, the electroluminescent medium comprises a hole-injection/hole-transport layer adjacent to the anode, an electron-injection/electron-transport layer adjacent to the cathode, and an emitter layer between the hole-injection/hole-transport layer and the electron-injection/electron-transport layer.

In yet another embodiment, the OLED can further comprise an additional layer adjacent to the top electrode. In a preferred embodiment, the layer comprises indium tin oxide.

Other OLED structures will be evident to those skilled in the art.

In one embodiment, a typical OLED is formed by starting with a semi-transparent bottom electrode deposited on a glass substrate. In one embodiment, the electrode is an anode. In another embodiment, the electrode is a cathode. In another embodiment, the top electrode is semi-transparent.

An anode is typically about 800 Å thick and can have one layer comprising a metal having a high work function, a metal oxide and mixtures thereof. Preferably, the anode comprises a material selected from the group consisting of a conducting or semiconducting metal oxide or mixed metal oxide such as indium zinc tin oxide, indium zinc oxide, ruthenium dioxide, molybdenum oxide, nickel oxide or indium tin oxide, a metal having a high work function, such as gold or platinum, and a mixture of a metal oxide and a metal having a high work function. In one embodiment, the anode further comprises a thin layer (approximately 5–15 Å thick) of dielectric material between the anode and the first hole-injection/hole-transport layer. Examples of such dielectric materials include, but are not limited to, lithium fluoride, cesium fluoride, silicon oxide and silicon dioxide. In another embodiment, the anode comprises a thin layer of an organic conducting material adjacent to the hole-injection/hole-transport layer. Such organic conducting materials include, but are not limited to, polyaniline, PEDOT-PSS, and a conducting or semi-conducting organic salt thereof.

A semi-transparent cathode is typically between 70 and 150 Å thick. In one embodiment, the cathode comprises a single layer of one or more metals, at least one of which has a low work function. Such metals include, but are not limited to, lithium, aluminum, magnesium, calcium, samarium, cesium and mixtures thereof. Preferably, the low work function metal is mixed with a binder metal, such as silver or indium. In another embodiment, the cathode further comprises a layer of dielectric material adjacent to the electron-injection/electron-transport layer, the dielectric material including, but not limited to, lithium fluoride, cesium fluoride, lithium chloride and cesium chloride. Preferably, the dielectric material is lithium fluoride or cesium fluoride. In preferred embodiments, the cathode comprises either aluminum and lithium fluoride, a mixture of magnesium and silver, or a mixture of lithium and aluminum. In yet another embodiment, the cathode comprises magnesium, silver and lithium fluoride.

In one embodiment, the hole-injection/hole-transport layer is about 750 Å thick. In a preferred embodiment, the hole-injection/hole-transport material comprises a compound of formula 1. In a particularly preferred embodiment, the hole-injection/hole-transport layer comprises a hole-injection layer comprising BPA-DNPB and a hole-transport layer comprising BPA-BCA.

In one embodiment, an OLED comprises an emitter layer between the electron-injection/electron-transport layer and the hole-injection/hole-transport layer in which electrons from the electron-injection/electron-transport layer and holes from the hole-injecting/hole-transport layer recombine. Depending on the composition of the emitter layer, OLEDs emit visible light of different colors. Emitter layers typically comprise at least one host compound, either alone or together with at least one dopant compound. Examples of host compounds include, but are not limited to, ALQ, IDE-120 and IDE-140 (Idemitsu Kosan Co., Ltd., Tokyo, Japan). Examples of dopant compounds include, but are not limited to, Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, quinacridone derivatives such as diethyl pentyl quinacridone and dimethyl quinacridone, distyrylamine derivatives, such as IDE-102, IDE-105 (Idemitsu Kosan Co., Ltd., Tokyo, Japan), rubrene, DCJTB, pyrromethane 546, and mixtures thereof. The structure of DCJTB is shown below:

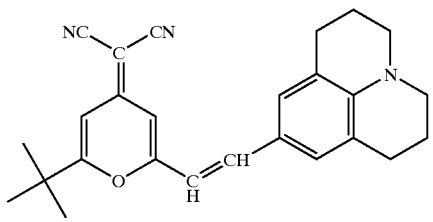

An emitter layer may be between 200–400 Å thick.

The electron-injection/electron-transport layer is typically about 350 Å thick and comprises a compound such as ALQ, or a suitable oxadiazole derivative. In a preferred embodiment, the electron-injection/electron-transport layer is ALQ.

In another embodiment, an OLED of the present invention comprises a 750 Å thick hole-injection/hole-transport layer of bis(N,N'-1-naphthyl-phenyl-amino-biphenyl)-1-naphthyl amine (NA-DNPB), a 750 Å thick emitter/electron transport layer of ALQ, and either Mg:Ag or LiF/Al cathode.

In a preferred embodiment, an OLED of the present invention comprises a 550 Å thick hole-injection layer of BPA-DNPB, a 200 Å thick hole-transport layer of BPA-BCA, a 350 Å thick emitter layer of ALQ doped with 2.5% of coumarin 6, a 300 Å thick electron transport layer of ALQ, and a cathode that is either Mg:Ag or aluminum on lithium fluoride.

In one preferred embodiment, an OLED of the present invention is a down-emitter that emits green light and comprises an anode comprising indium tin oxide, a hole-injection layer adjacent to the anode comprising BPA-DNPB, a hole-transport layer adjacent to the hole-injection layer comprising BPA-BCA, an emitter layer adjacent to the hole-transport layer comprising ALQ and a compound selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, and mixtures thereof, an electron-transport layer adjacent to the emitter layer comprising ALQ, and a cathode comprising either lithium fluoride and aluminum or magnesium and silver.

In another preferred embodiment, an OLED of the present invention is an up-emitter that emits green light and comprises an anode comprising molybdenum oxide, a hole-injection layer adjacent to the anode comprising BPA-DNPB, a hole-transport layer adjacent to the hole-injection layer comprising BPA-BCA, an emitter layer adjacent to the hole-transport layer comprising ALQ and a compound selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, and mixtures thereof, an electron-transport layer adjacent to the emitter layer comprising ALQ, and a cathode comprising lithium fluoride, magnesium and silver.

In yet another preferred embodiment, an OLED of the present invention emits white or blue light and comprises an anode comprising indium tin oxide, a hole-injection layer adjacent to the anode comprising BPA-DNPB, a hole-transport layer adjacent to the hole-injection layer comprising BPA-B CA, an emitter layer adjacent to the hole-transport layer comprising DCJTB, IDE-102 and IDE-120, an electron-transport layer adjacent to the emitter layer comprising ALQ, and a cathode comprising lithium fluoride and aluminum.

In a preferred embodiment of the present invention, the OLED display device is a microdisplay. A microdisplay is a display device that is not viewable by the unaided eye, and therefore requires the use of an optic. Preferably, the subpixel size of a microdisplay device is less than about 15 microns, more preferably less than about 5 microns, and most preferably between about 2 microns and about 3 microns.

The multi-layered OLED devices of the invention allow for a "staircase" change in the energy difference of electrons and holes as they travel from the electrodes through each layer toward the emitter layer, where they recombine to emit light. Typically, the anode and cathode of an OLED have an energy difference of about 1.6–1.8 eV. A typical band gap of electrons and holes in the emitter layer is about 2.7 eV–2.9 eV, so that radiation emission resulting from recombination is in the visible light region (1.75 to 3 eV). In the present invention, the increase in energy difference of holes and electrons from the anode and cathode to the emitter layer is accomplished incrementally as the electrons and holes travel through the layers between the electrodes and the emitter layer. The energy difference is increased in increments of about 0.2–0.3 eV per layer to achieve the resulting band gap of 2.7 eV–2.9 eV in the emitter layer. A staircase change in energy provides for a lower operating voltage and better efficiency of operation of the OLED device, resulting in a higher quantum yield of luminescence for a given current density.

Hole-injection and Hole-transport Materials

The present invention relates to OLEDs having incorporated in the electroluminescent medium organic compounds with variable ionization potentials (IP) and electron affinities (EA) and high glass transition temperatures. Specifically, the present invention relates to OLEDs having hole-injection and hole-transport layers with variable IP and high glass transition temperatures. In particular, the present invention relates to OLEDs having hole-injection and hole-transport layers comprising a compound of formula 1:

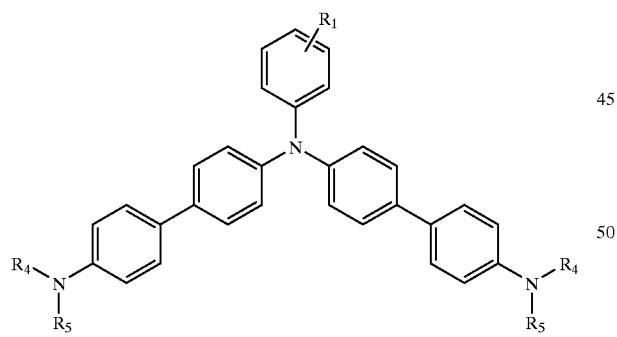

(1)

wherein $R_1$ is selected from the group consisting of biphenyl, naphthyl, phenyl and

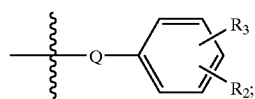

Q is selected from the group consisting of a bond, $C_1$–$C_4$ alkyl, —C(O)—, —S(O)—, —O—Si—O—, —O—Ge—O—, —O—,

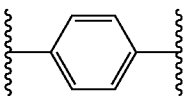

and $R_2$ and $R_3$ are each independently selected from the group consisting of aryl, F, Cl, —$CF_3$, saturated alkyl of up to 10 carbon atoms, preferably of between 1 and 4 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein the fused polycyclic aromatic system comprises up to 16 carbon atoms;

$R_4$ and $R_5$ are each independently selected from the group consisting of:

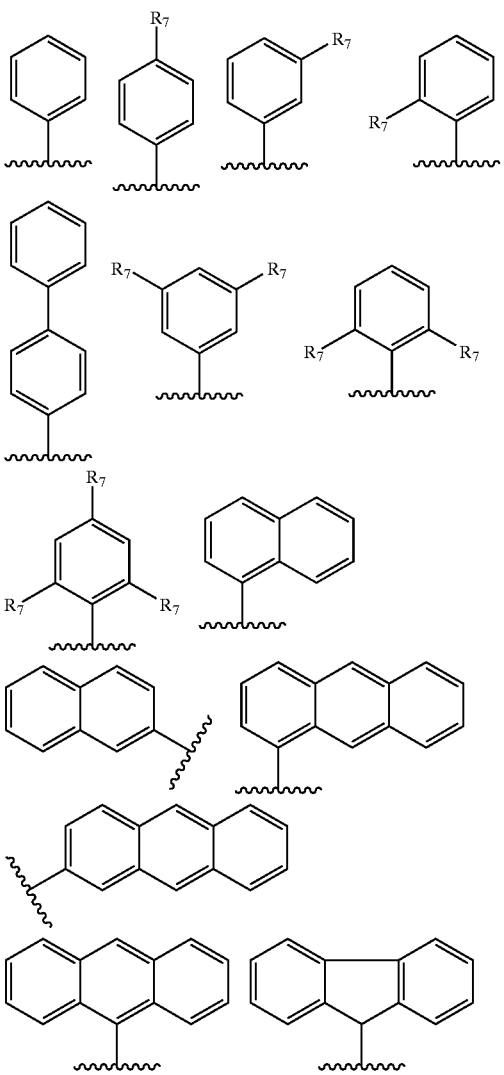

-continued

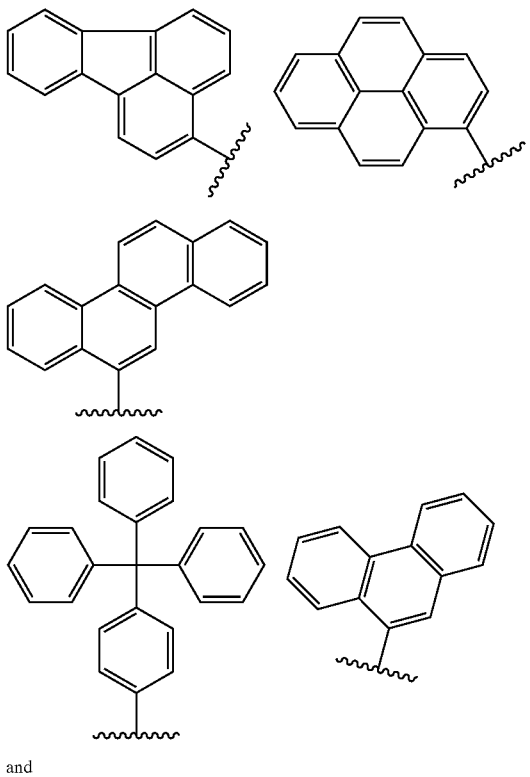

and

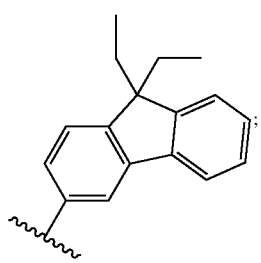

or R₄ and R₅ taken together with the nitrogen to which they are attached are selected from the group consisting of:

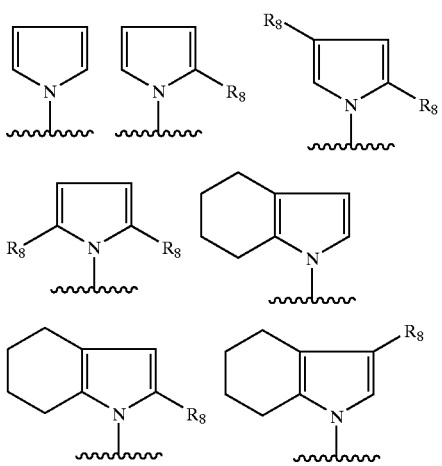

-continued

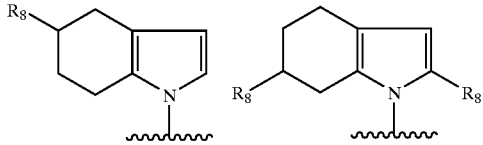

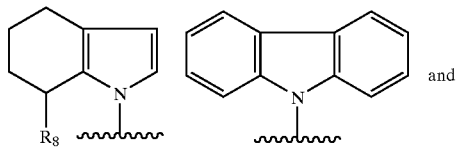

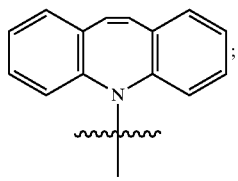
and $R_6$ is $C_1$–$C_4$ straight or branched saturated alkyl;

$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and $R_9$ is selected from the group consisting of $C_1$–$C_6$ alkyl and aryl.

Additional compounds for this embodiment include compounds of formula 1, wherein $R_4$ and $R_5$ are each independently selected from the group consisting of:

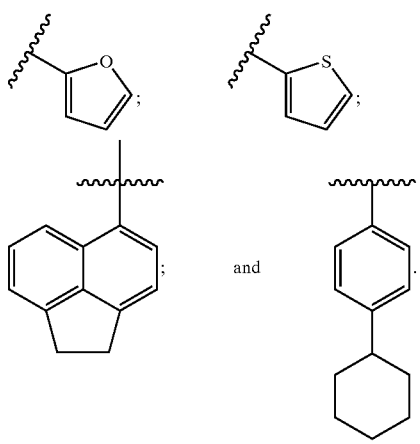

Such OLEDs incorporating organic compounds with variable IP and high glass transition temperatures in the hole-injection and hole-transport layers are longer-lived and can withstand higher temperatures than OLEDs that incorporate traditional triarylamines in those layers. The variable IP of these materials also permits staircase tuning of the hole energies to increase the quantum efficiency of the OLEDs. Hole-injection and hole-transport layers comprising a compound of formula 1 typically have glass transition temperatures in the range of 130–180° C. Therefore, the OLEDs of the present invention can be operated at higher current densities, which results in increased brightness, without changing the morphology of the hole-injection and hole-transport layers and degrading the device.

Synthesis of Hole-injection and Hole-transport Compounds

Hole-injection and hole-transport compounds useful in OLEDs of the present invention can be made as shown in Scheme I.

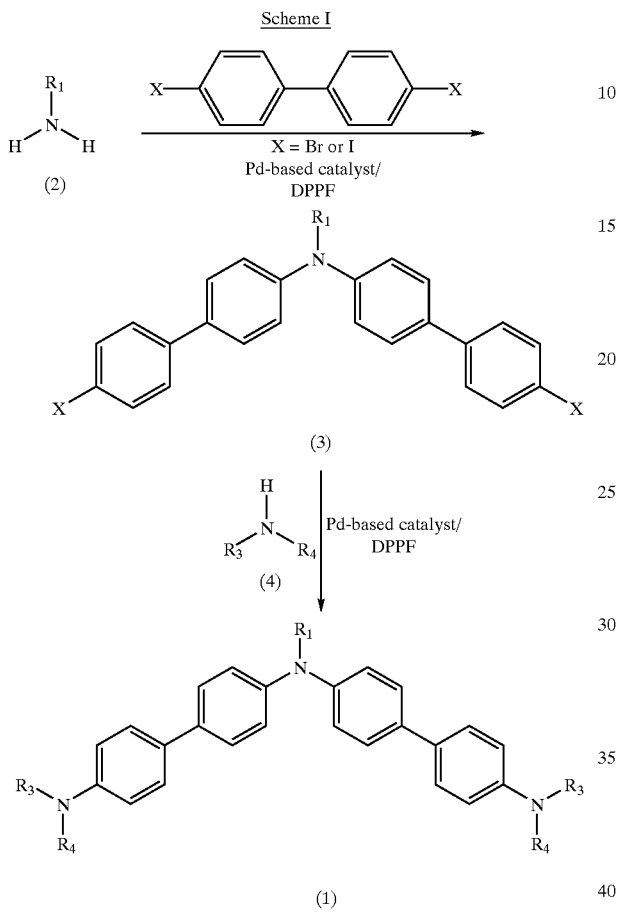

In a first step in an inert atmosphere dry box, about 0.5 equivalents of diphenylphosphino ferrocene (DPPF) and about 0.35 equivalents of tris(dibenzylideneacetone) dipalladium ($Pd_2(dba)_3$) are added to a solution comprising about 10 equivalents of a compound of formula 2, about 25 equivalents of 4,4'-dibromobiphenyl or 4,4'-diiodobiphenyl and about 22 equivalents of sodium tert-butoxide in anhydrous toluene. The reaction mixture is then heated to about 95° C. for about 20 hours. Upon completion of the reaction, the solution is cooled to room temperature, organic solvent is removed by rotary evaporation and a compound of formula 3 is isolated by silica gel chromatography using gel of 230–400 mesh and hexane as the eluant. The reaction yield ranges from 70% to 95%, depending upon the selection of $R_1$. Mass spectroscopic analysis may be used to confirm the formation of the compound of formula 3.

In a second step in an inert atmosphere dry box, catalytic amounts of DPPF and $Pd_2(dba)_3$ are added to a solution of the compound of formula 3 and sodium tert-butoxide dissolved in anhydrous toluene. To this solution is added 4 equivalents of a compound of formula 4 dissolved in toluene. The reaction mixture is heated to about 95° C. for about 20 hours. Upon completion of the reaction, the solution is cooled to room temperature, organic solvent is removed by rotary evaporation and a compound of formula 1 is isolated by silica gel chromatography. Reaction yields range from 75% to 95%. The product may be further purified by sublimation. Elemental and mass spectroscopic analyses are used to confirm the formation of the compounds of formula 1.

The thermal properties and glass transition temperatures of compounds of formula 1 are determined using differential scanning calorimetry (DSC) and thermo gravimetric analysis (TGA).

EXAMPLES

Example 1

Synthesis of BPA-BCA

Materials

Silica gel having average particle size of 230–400 mesh from Whatman was used in a 20 cm column for purification. Compounds were eluted using 5% $CH_2Cl_2$ in hexane as the mobile phase.

Sublimation was performed using a train sublimation apparatus designed in the laboratory at a pressure of $1.0 \times 10^{-6}$ torr and at temperature of 350 ° C.

Mass spectroscopy was performed on a SFNNIGAN 4500 instrument from Sfnnigan Corporation using direct ionization with methane as the gas at a pressure of 0.4 millitorr.

TGA was performed on a TGA-50 instrument from Shimadzu.

DSC was performed using a DSC-50 instrument from Shimadzu.

All starting materials and solvents for the syntheses were of pure grade and were used without further purification.

Methods

In an inert atmosphere box, catalytic amounts of diphenylphosphino ferrrocene (DPPF) (285 mg) and tris (dibenzylideneacetone) dipalladium ($Pd_2(dba)_3$) (312 mg) were added to a solution of 0.85 g (1 eq) of diphenylamine, 4.70 g (3 eq) of 4,4'-dibromobiphenyl and 1.05 g (2.2 eq) of sodium tert-butoxide in anhydrous toluene. The reaction mixture was heated at 95° C. for 30 hours. The reaction solution was cooled to room temperature, organic solvent was removed by rotary evaporation, and biphenylamino-bis-biphenyl bromide (BPA-BPBBr) (5) was isolated by silica gel chromatography (see Materials, above). 2.80 g (0.89 eq) of BPA-BPBBr was obtained after separation, giving a reaction yield of 89%. Mass spectroscopic analysis (see Materials, above) confirmed the formation of (5)

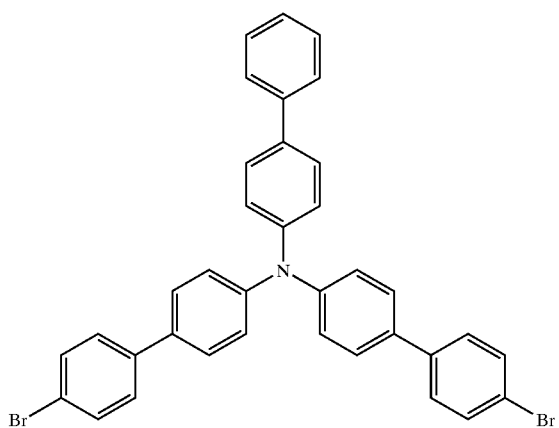

In an inert atmosphere box, 0.35 mmol (320 mg) of Pd$_2$(dba)$_3$ and 0.5 mmol (280 mg) of DPPF were added to a solution of 2 mmol (1.26 g) of BPA-BPBBr (5) and 5.5 mmol (0.55 g) of sodium tert-butoxide dissolved in 25 mL of anhydrous toluene. 5.0 mmol (0.85 g) of carbazole dissolved in 20 mL of toluene were added to this solution. The reaction mixture was heated at 95° C. for 30 hours. Upon completion of the reaction, the solution was cooled to room temperature, organic solvent was removed by rotary evaporation, and the product BPA-BCA (6) was isolated by silica gel chromatography (see Materials, above). 1.29 g of crude product was obtained (80% yield). BPA-BCA was further purified by sublimation (see Materials, above). Mass spectroscopic (see Materials, above) analysis confirmed the formation of BPA-BCA. The glass transition temperature ($T_g$) was determined by DSC (see Materials, above) to be about 162° C.

of 0.74 g (1 eq) of 1-aminonaphthalene, 4.70 g (3 eq) of 4,4'-dibromobiphenyl and 1.05 g (2.2 eq) of sodium tert-butoxide in anhydrous toluene. The reaction mixture was heated at 95° C. for 30 hours. The reaction solution was cooled to room temperature, organic solvent was removed by rotary evaporation, and 1-naphthyl-amino-bis-biphenyl bromide (NA-BPBBr) (7) was isolated by silica gel chromatography (see Materials, Example 1, above). 2.54 g (0.84 eq) of NA-BPBBr (7) was obtained after separation, giving a reaction yield of 84%. Mass spectroscopic analysis (see Materials, Example 1, above) confirmed the formation of NA-BPBBr (7).

(7)

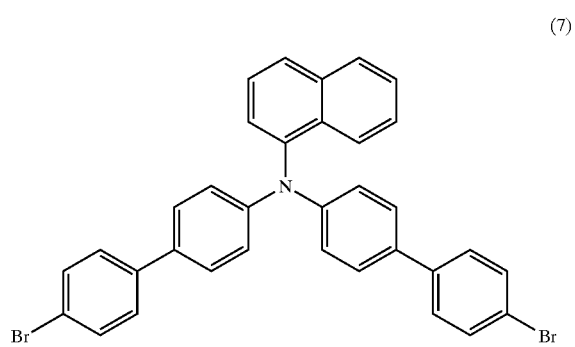

In an inert atmosphere box, 0.35 mmol (320 mg) of Pd$_2$(dba)$_3$ and 0.5 mmol (280 mg) of DPPF were added to a solution of 2 mmol (1.216 g) of NA-BPBBr (7) and 5.5 mmol (0.55 g) of sodium tert-butoxide dissolved in 25 mL of anhydrous toluene. 5.0 mmol (1.1 g) of phenylnaphthyl dissolved in 20 mL of toluene were added to this solution. The reaction mixture was heated at 95° C. for 30 hours. Upon completion of the reaction, the solution was cooled to room temperature, organic solvent was removed by rotary evaporation, and the product NA-DNPB (8) was isolated by (6)

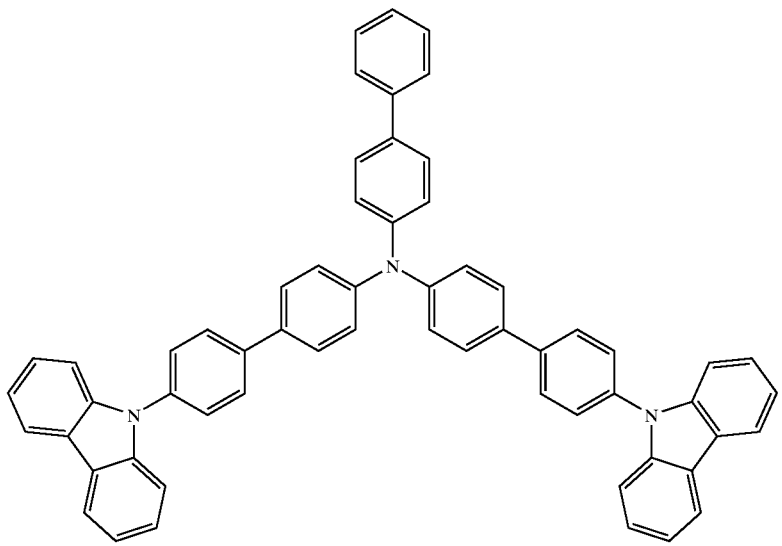

Example 2

Synthesis of NA-DNPB

In an inert atmosphere box, catalytic amounts of DPPF (285 mg) and Pd$_2$(dba)$_3$ (312 mg) were added to a solution silica gel chromatography (see Materials, Example 1, above). 1.5 g of crude product was obtained (85% yield). NA-DNPB (8) was further purified by sublimation (see Materials, Example 1, above). Mass spectroscopic analysis (see Materials, Example 1, above) confirmed the formation of NA-DNPB (8). The glass transition temperature ($T_g$) was determined by DSC (see Materials, Example 1, above) to be about 147° C.

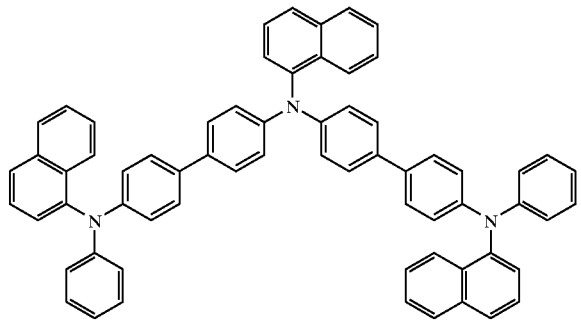

(8)

Example 3

Synthesis of Bis(carbazol-n-biphenyl)-1-naphthyl Amine (NA-BCA)

NA-BPBBr was synthesized as described above in Example 2.

In an inert atmosphere dry box, 0.35 mmol (320 mg) of $Pd_2(dba)_3$ and 0.5 mmol (280 mg) of DPPF were added to a solution of 2 mmol (1.216 g) of NA-BPBBr (7) and 5.5 mmol (0.55 g) of sodium tert-butoxide dissolved in 25 mL of anhydrous toluene. 5.0 mmol (0.85 g) of carbazole dissolved in 20 mL of toluene were added to this solution. The reaction mixture was heated at 95° C. for 30 hours. Upon completion of the reaction, the solution was cooled to room temperature, organic solvent was removed by rotary evaporation, and the product NA-BCA (9) was isolated by silica gel chromatography (see Materials, Example 1, above). 1.20 g of crude product was obtained (85% yield). NA-BCA (9) was further purified by sublimation (see Materials, Example 1, above). Mass spectroscopic analysis (see Materials, Example 1, above) confirmed the formation of NA-BCA (9).

Example 4

Formation of an OLED Using BPA-BCA as Hole-injection and Hole-transport Layers

A 750 Å thick hole-injection/hole-transport layer of BPA-BCA was thermally evaporated on pre-cleaned indium tin oxide (ITO) substrate in high vacuum ($10^{-6}$–$10^{-7}$ torr) at room temperature. This was followed by evaporation of a 750 Å thick emitter/electron transport layer of ALQ. A cathode comprising a 7.5 Å layer of LiF followed by a 500 Å layer of Al was then deposited. The resulting OLED demonstrated diode behavior and emitted green light when direct voltage was applied. The OLED demonstrated quantum efficiency of 5.2 cd/A and 1.6% ph/e, a low driving voltage (6.8 Volts) at a current density of 20 mA/cm$^2$, and a brightness level of 590 cd/m$^2$ for green emission.

Example 5

Formation of an OLED Using NA-DNPB as Hole-injection and Hole-transport Layers

A 750 Å thick hole-injection/hole-transport layer of NA-DNPB was thermally evaporated on pre-cleaned indium tin oxide (ITO) substrate that has been ashed in oxygen plasma (400 W power, 300 millitorr pressure, oxygen flow 50 cc/min) for one minute (see Example 4, above). This was followed by evaporation of a 750 Å thick emitter/electron transport layer of ALQ and a either a Mg:Ag or LiF/Al cathode (see Example 4, above). The resulting OLED demonstrated diode behavior and emitted green light when direct voltage was applied. The OLED demonstrated quantum efficiency of 2.95 cd/A and 0.91% ph/e, a low driving voltage (7.4 Volts) at a current density of 20 InA/cm$^2$, and a brightness level of 1053 cd/m$^2$ for green emission.

Example 6

Formation of an OLED Using BPA-DNPB as Hole-injection Layer and BPA-BCA as Hole-transport Layer A 550 Å thick hole-injection layer of BPA-DNPB was thermally evaporated on pre-cleaned indium tin oxide (ITO)

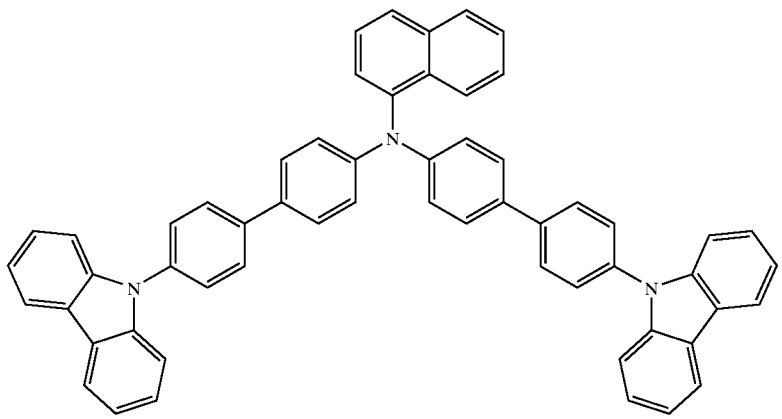

(9)

substrate in high vacuum (see Example 5, above). This was followed by evaporation of a 200 Å thick hole-transport layer of BPA-BCA, evaporation of a 350 Å thick emitter layer of ALQ doped with 2.5% of coumarin 6 (see Example 4, above), and evaporation of a 300 Å thick electron transport layer of ALQ, and a LiF/Al cathode (see Example 4, above). The resulting OLED demonstrated diode behavior and emitted green light when direct voltage was applied. The OLED demonstrated quantum efficiency of 14.3 cd/A and 4.0% ph/e, a low driving voltage (7.0 Volts) at a current density of 20 mA/cm$^2$, and a brightness level of 2,900 cd/m$^2$ for green emission.

References Cited

All references cited herein are incorporated herein by reference in their entirety and for all purposes to the same extent as if each individual publication or patent or patent application was specifically and individually indicated to be incorporated by reference in its entirety for all purposes as fully set forth.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An organic light emitting diode device comprising:
   (a) a cathode;
   (b) an anode; and
   (c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

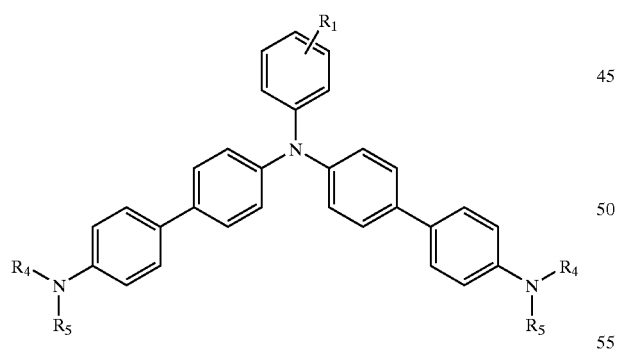

(1)

wherein $R_1$ is selected from the group consisting of biphenyl, naphthyl, phenyl and

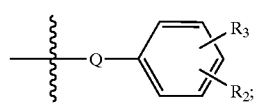

Q is selected from the group consisting of a bond, $C_1$-$C_4$ alkyl, —C(O)—, —S(O)—, —O—Si—O—, —O—Ge—O—, —O—,

and

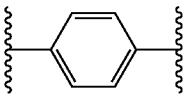

$R_2$ and $R_3$ are each independently selected from the group consisting of aryl, F, Cl, —CF$_3$, saturated alkyl of up to 10 carbon atoms, SO$_2$R$_6$, Si(R$_6$)$_3$, and OR$_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of:

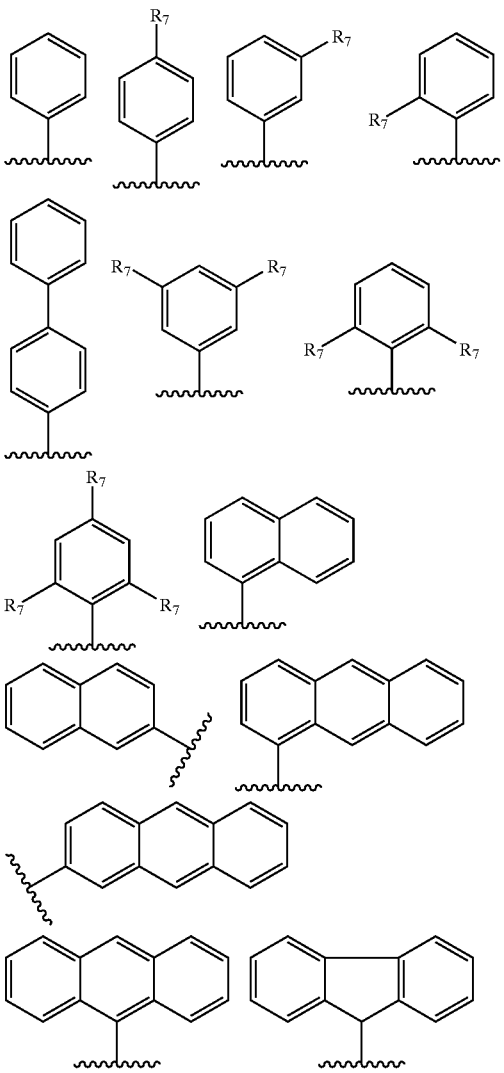

-continued

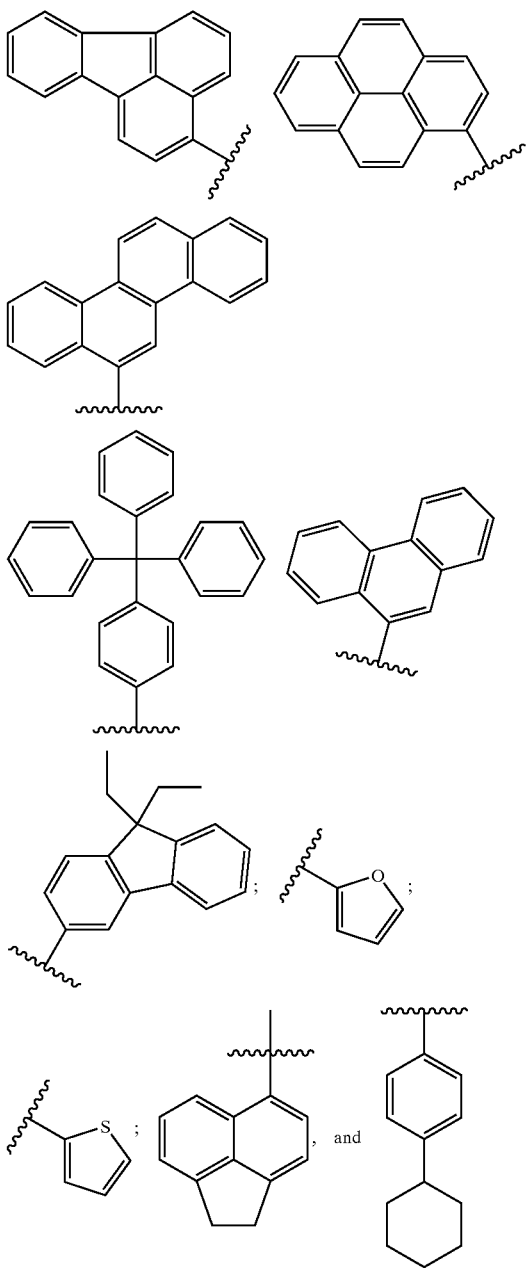

or $R_4$ and $R_5$ taken together with the nitrogen to which they are attached are selected from the group consisting of:

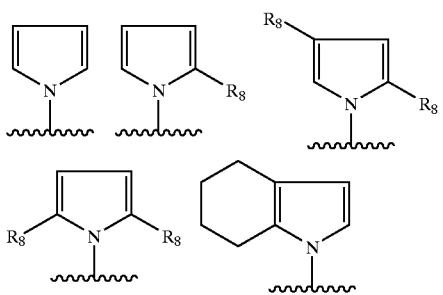

-continued

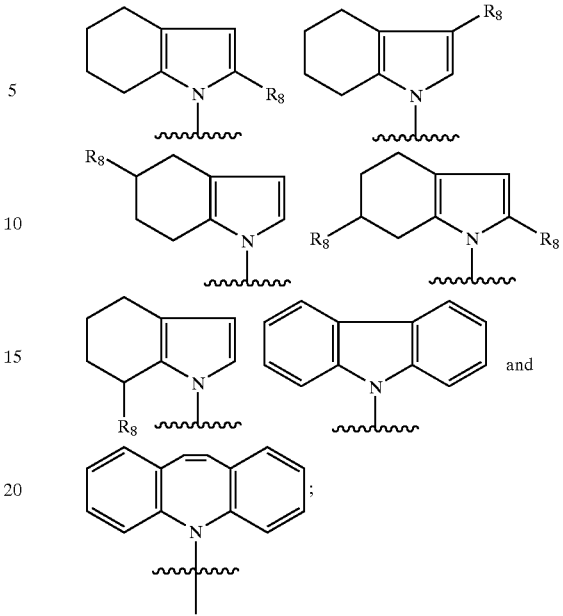

$R_6$ is $C_1$–$C_4$ straight or branched saturated alkyl;
$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$;
$R_9$ is selected from the group consisting of $C_1$–$C_6$ alkyl and aryl.

2. The device of claim 1, wherein said $R_1$ is

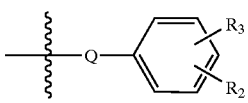

and $R_2$ and $R_3$ are each independently alkyls of between 1 and 4 carbon atoms.

3. The device of claim 1, wherein said anode is a bottom electrode and said cathode is a top electrode.

4. The device of claim 1, wherein said anode is semi-transparent.

5. The device of claim 1, wherein said cathode is semi-transparent.

6. The device of claim 3, wherein said anode comprises a metal having a high work function, a metal oxide or mixtures thereof.

7. The device of claim 6, wherein said anode comprises a material selected from the group consisting of indium tin oxide, indium zinc tin oxide, indium zinc oxide, ruthenium dioxide, molybdenum oxide, nickel oxide and mixtures thereof.

8. The device of claim 7, wherein said anode comprises indium tin oxide.

9. The device of claim 3, wherein said anode further comprises a layer of dielectric material adjacent to said second organic layer.

10. The device of claim 9, wherein said dielectric material is selected from the group consisting of lithium fluoride, cesium fluoride, silicon oxide and silicon dioxide.

11. The device of claim 3, wherein said anode further comprises a layer of organic conducting material adjacent to said second organic layer.

12. The device of claim 11, wherein said organic conducting material is selected from the group consisting of polyaniline, PEDOT-PSS, and a conducting or semiconducting organic salt thereof.

13. The device of claim 3, wherein said cathode comprises a material having a low work function.

14. The device of claim 13, wherein the material having a low work function is selected from the group consisting of aluminum, magnesium, calcium, samarium, lithium, cesium, and mixtures thereof.

15. The device of claim 14, wherein said cathode comprises lithium and aluminum.

16. The device of claim 14, wherein said cathode further comprises a layer of dielectric material adjacent to said first organic layer formed from at least one electron-injection/electron-transport material.

17. The device of claim 16, wherein said dielectric material is selected from the group consisting of lithium fluoride, cesium fluoride, lithium chloride and cesium chloride.

18. The device of claim 17, wherein the cathode comprises magnesium and lithium fluoride and further comprises silver.

19. The device of claim 17, wherein the cathode comprises aluminum and lithium fluoride.

20. The device of claim 3, wherein said at least one hole-injection/hole-transport material comprises a compound selected from the group consisting of BPA-BCA, NA-DNPB, NA-BCA and mixtures thereof.

21. The device of claim 3, further comprising an emitter layer between said first organic layer and said second organic layer.

22. The device of claim 21, wherein said emitter layer comprises a host compound.

23. The device of claim 22, wherein said host compound is selected from the group consisting of ALQ and IDE-102.

24. The device of claim 21, wherein said emitter layer further comprises a dopant compound.

25. The device of claim 24, wherein said dopant compound is selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, a quinacridone derivative, a distyrylamine derivative, IDE-102, rubrene, DCJTB, pyrromethane 546, and mixtures thereof.

26. The device of claim 3, wherein said at least one electron-injection/electron-transport material comprises a compound selected from the group consisting of ALQ, and an oxadiazole derivative.

27. The device of claim 26, wherein said at least one electron-injection/electron-transport material is ALQ.

28. The device of claim 3, wherein said device is a microdisplay device.

29. An organic light emitting diode device comprising:
(a) a cathode;
(b) an anode;
(c) a layer formed from at least one electron-injection/electron-transport material that is adjacent to said cathode;
(d) a hole-injection layer that is adjacent to said anode; and
(e) at least one hole-transport layer that is adjacent to said hole-injection layer, wherein at least one of said hole-injection and hole-transport layers comprises a compound of formula 1:

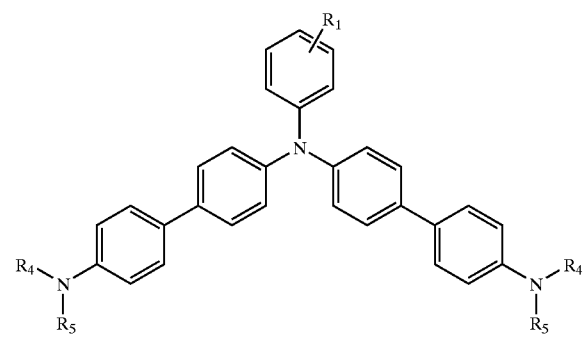

wherein $R_1$ is selected from the group consisting of biphenyl, naphthyl, phenyl and

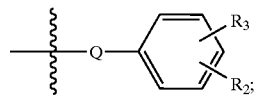

Q is selected from the group consisting of a bond, $C_1$-$C_4$ alkyl, —C(O)—, —S(O)—, —O—Si—O—, —O—Ge—O—, —O—,

and

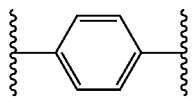

$R_2$ and $R_3$ are each independently selected from the group consisting of aryl, F, Cl, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of:

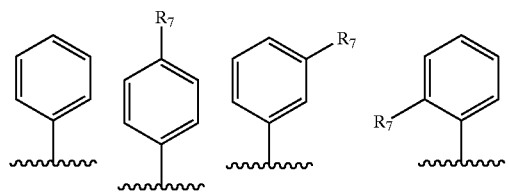

-continued
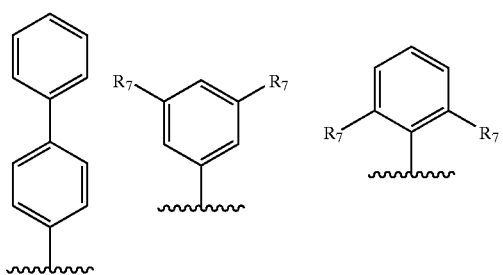
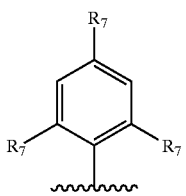
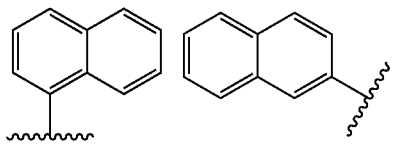
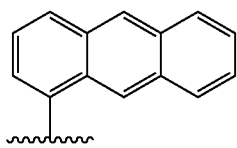
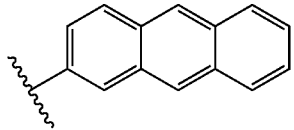
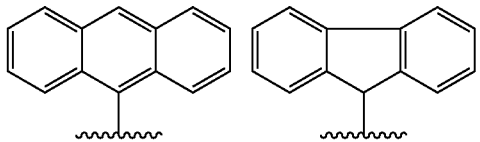
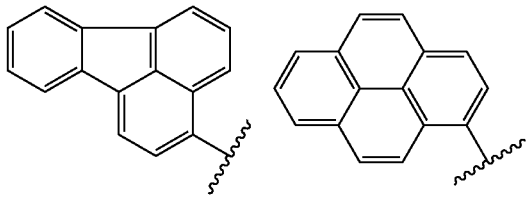
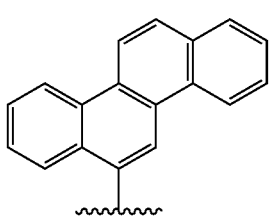
-continued
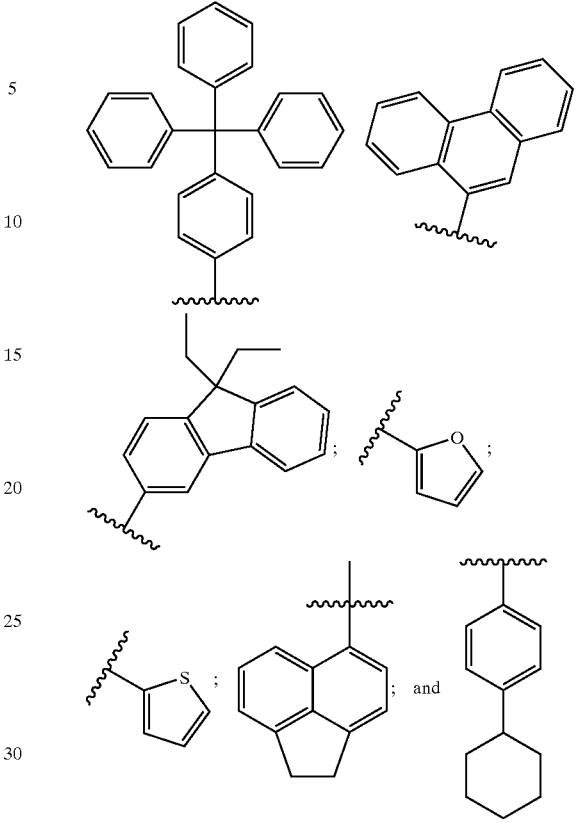
or $R_4$ and $R_5$ taken together with the nitrogen to which they are attached are selected from the group consisting of:
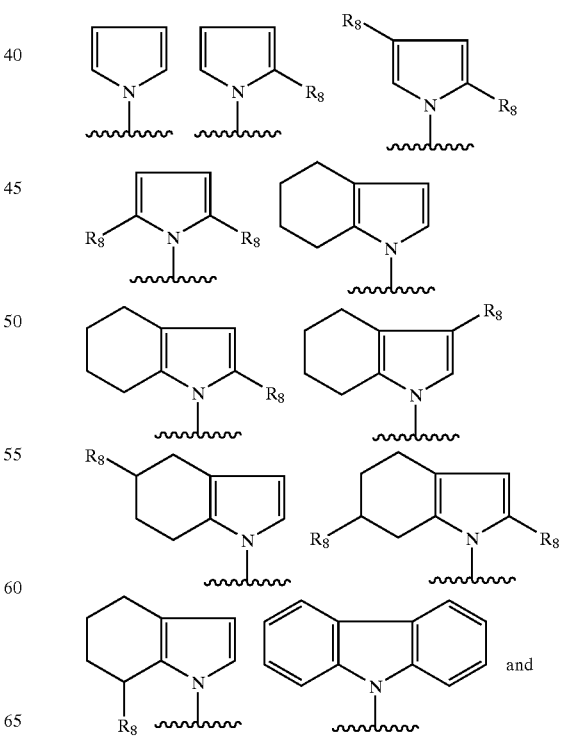

-continued

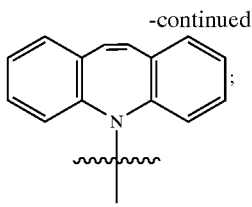

R$_6$ is C$_1$–C$_4$ straight or branched saturated alkyl;

R$_7$ and R$_8$ are each independently selected from the group consisting of —OR$_9$, C$_1$–C$_4$ alkyl, aryl, —SCH$_3$, —CF$_3$, —Cl, —Br, —NO$_2$, and —COOR$_9$; and R$_9$ is selected from the group consisting of C$_1$–C$_6$ alkyl and aryl.

30. The device of claim 29, wherein said anode is a bottom electrode and said cathode is a top electrode.

31. The device of claim 29, wherein said anode is semi-transparent.

32. The device of claim 29, wherein said cathode is semi-transparent.

33. The device of claim 30, wherein said anode comprises a metal having a high work function, a metal oxide or mixtures thereof.

34. The device of claim 33, wherein said anode comprises a material selected from the group consisting of indium tin oxide, indium zinc tin oxide, indium zinc oxide, ruthenium dioxide, molybdenum oxide, nickel oxide and mixtures thereof.

35. The device of claim 34, wherein said anode comprises indium tin oxide.

36. The device of claim 30, wherein said anode further comprises a layer of dielectric material adjacent to said second hole-injection layer.

37. The device of claim 36, wherein said dielectric material is selected from the group consisting of lithium fluoride, cesium fluoride, silicon oxide and silicon dioxide.

38. The device of claim 30, wherein said anode further comprises a layer of organic conducting material adjacent to said hole-injection layer.

39. The device of claim 38, wherein said organic conducting material is selected from the group consisting of polyaniline, PEDOT-PSS, and a conducting or semi-conducting organic salt thereof.

40. The device of claim 30, wherein said cathode comprises a material having a low work function.

41. The device of claim 40, wherein the material having a low work function is selected from the group consisting of aluminum, magnesium, calcium, samarium, lithium, cesium, and mixtures thereof.

42. The device of claim 41, wherein said cathode comprises lithium and aluminum.

43. The device of claim 30, wherein said cathode further comprises a layer of dielectric material adjacent to said layer formed from at least one electron-injection/electron-transport material.

44. The device of claim 43, wherein said dielectric material is selected from the group consisting of lithium fluoride, cesium fluoride, lithium chloride and cesium chloride.

45. The device of claim 44, wherein the cathode comprises magnesium and lithium fluoride and further comprises silver.

46. The device of claim 44, wherein the cathode comprises aluminum and lithium fluoride.

47. The device of claim 30, wherein at least one of said hole-injection and hole-transport layers comprises a compound selected from the group consisting of BPA-BCA, NA-DNPB, NA-BCA and mixtures thereof.

48. The device of claim 47, wherein the hole-injection layer comprises BPA-DNPB and the at least one hole transport layer comprises BPA-BCA.

49. The device of claim 30, further comprising an emitter layer between said organic layer formed from at least one electron-injection/electron-transport material and said at least one hole-transport layer.

50. The device of claim 49, wherein said emitter layer comprises a host compound.

51. The device of claim 50, wherein said host compound is selected from the group consisting of ALQ and IDE-102.

52. The device of claim 50, wherein said emitter layer further comprises a dopant compound.

53. The device of claim 52, wherein said dopant compound is selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545, a quinacridone derivative, a distyrylamine derivative, IDE-102, rubrene, DCJTB, pyrromethane 546, and mixtures thereof.

54. The device of claim 30, wherein said at least one electron-injection/electron-transport material comprises a compound selected from the group consisting of ALQ, and an oxadiazole derivative.

55. The device of claim 54, wherein said at least one electron-injection/electron-transport material is ALQ.

56. The device of claim 30, further comprising a first hole-transport layer and a second hole-transport layer.

57. The device of claim 56, wherein at least two of the first hole-transport layer, the second hole-transport layer and the hole-injection layer are inter-deposited.

58. The device of claim 30, wherein said device is a microdisplay device.

59. The device of claim 29, wherein R$_1$ is

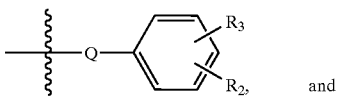

and

R$_2$ and R$_3$ are each independently alkyls of between 1 and 4 carbon atoms.

60. An organic light-emitting diode device that emits green light, comprising:

(a) a bottom electrode that is an anode comprising indium tin oxide;

(b) a hole-injection layer adjacent to said anode comprising BPA-DNPB;

(c) a hole-transport layer adjacent to said hole-injection layer comprising BPA-BCA;

(d) an emitter layer adjacent to said hole-transport layer comprising ALQ and a compound selected from the group consisting of Coumarin 6, Coumarin 485, Coumarin, 487, Coumarin 490, Coumarin 498, Coumarin 500, Coumarin 503, Coumarin 504, Coumarin 504T, Coumarin 510, Coumarin 515, Coumarin 519, Coumarin 521, Coumarin 521T, Coumarin 522B, Coumarin 523, Coumarin 525, Coumarin 535, Coumarin 540A, Coumarin 545 and mixtures thereof;

(e) an electron-transport layer adjacent to said emitter layer comprising ALQ; and (f) a top electrode that is a cathode comprising lithium fluoride and aluminum or magnesium and silver.

61. An organic light-emitting diode device that emits white or blue light, comprising:

(a) a bottom electrode that is an anode comprising indium tin oxide;

(b) a hole-injection layer adjacent to said anode comprising BPA-DNPB;

(c) a hole-transport layer adjacent to said hole-injection layer comprising BPA-BCA;

(d) an emitter layer adjacent to said hole-transport layer comprising DCJTB, IDE-120 and IDE-102;

(e) an electron-transport layer adjacent to said emitter layer comprising ALQ; and (f) a top electrode that is a cathode comprising aluminum and lithium fluoride.

62. A microdisplay device, comprising:

(a) at least one bottom electrode that is an anode;

(b) at least one top electrode that is a cathode; and (c) at least two organic layers between said at least one bottom electrode and said at least one top electrode, wherein said at least two organic layers comprise a first organic layer formed from at least one electron-injection/electron-transport material that is adjacent to said at least one cathode and a second organic layer formed from at least one hole-injection/hole-transport material that is adjacent to said at least one anode, said at least one hole-injection/hole-transport material comprising a compound of formula 1:

(1)

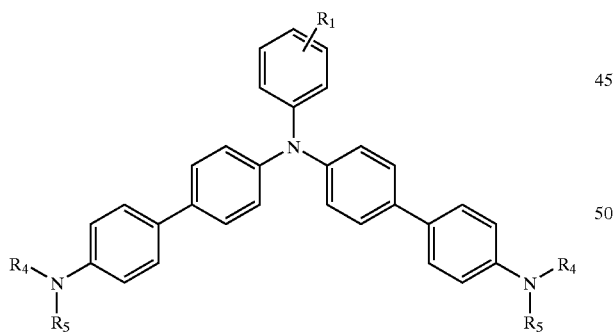

wherein $R_1$ is selected from the group consisting of biphenyl, naphthyl, phenyl and

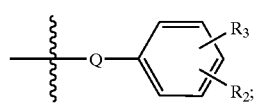

Q is selected from the group consisting of a bond, $C_1$-$C_4$ alkyl, —C(O)—, —S(O)—, —O—Si—O—, —O—Ge—O—, —O—,

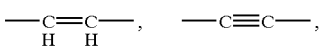

and

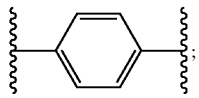

$R_2$ and $R_3$ are each independently selected from the group consisting of aryl, F, Cl, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of:

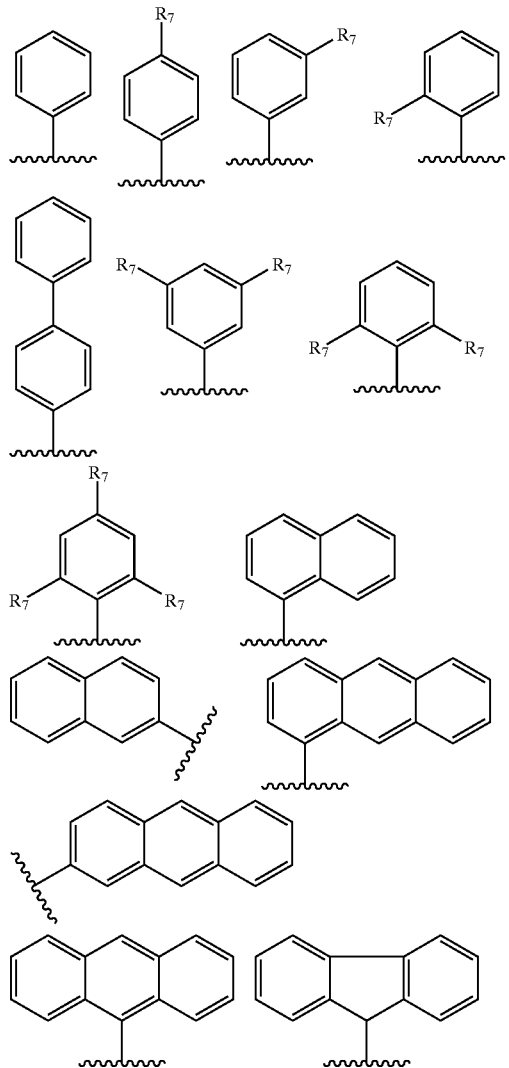

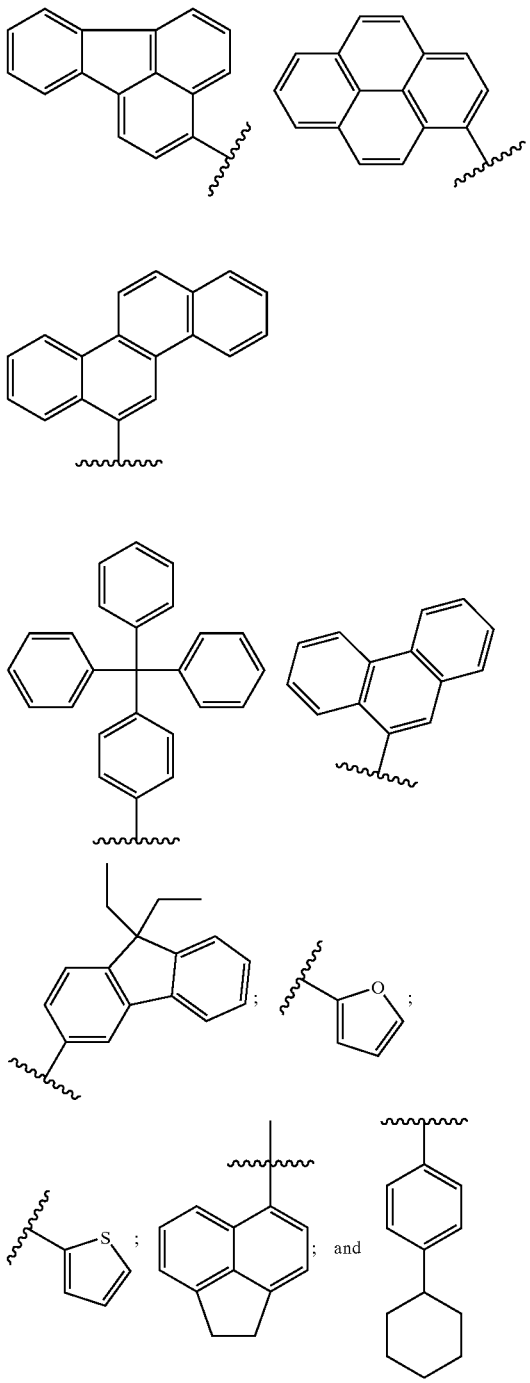

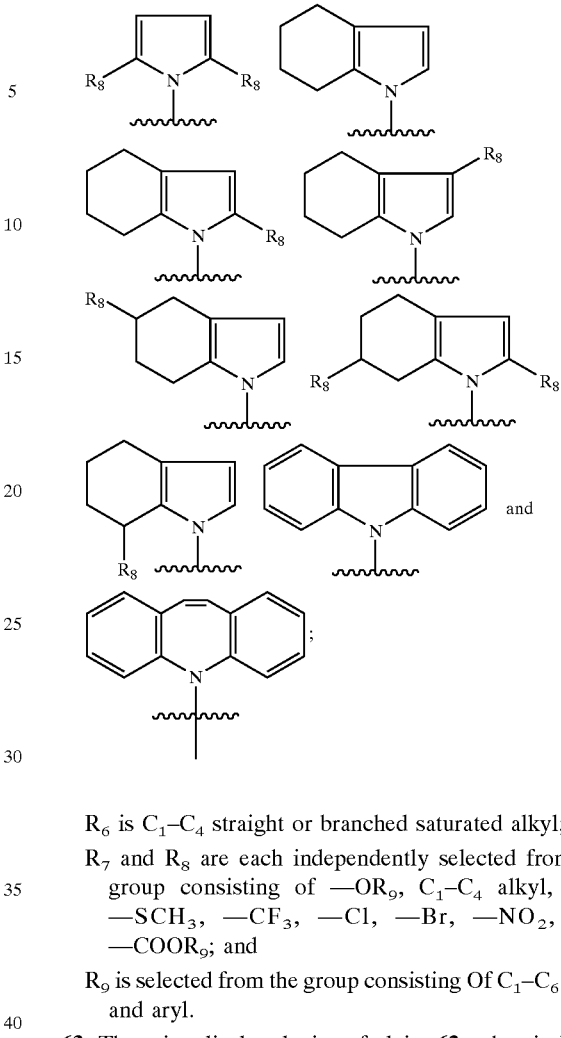

or $R_4$ and $R_5$ taken together with the nitrogen to which they are attached are selected from the group consisting of:

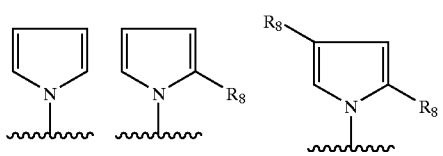

$R_6$ is $C_1-C_4$ straight or branched saturated alkyl;

$R_7$ and $R_8$ are each independently selected from the group consisting of $-OR_9$, $C_1-C_4$ alkyl, aryl, $-SCH_3$, $-CF_3$, $-Cl$, $-Br$, $-NO_2$, and $-COOR_9$; and $R_9$ is selected from the group consisting Of $C_1-C_6$ alkyl and aryl.

63. The microdisplay device of claim 62, wherein $R_1$ is

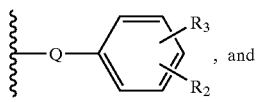, and $R_2$ and $R_3$ are each independently alkyls of 1 to 4 carbon atoms.

64. An organic light emitting diode device comprising:

(a) a cathode;

(b) an anode; and (c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

(1)

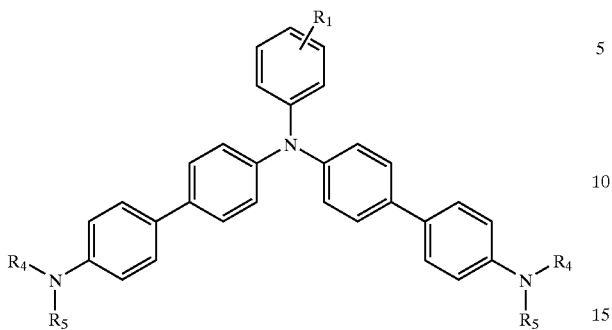

wherein $R_1$ is selected from the group consisting of biphenyl, naphthyl, and phenyl;

$R_2$ and $R_3$ are each independently selected from the group consisting of aryl, F, Cl, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of:

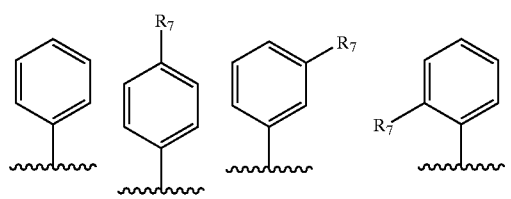

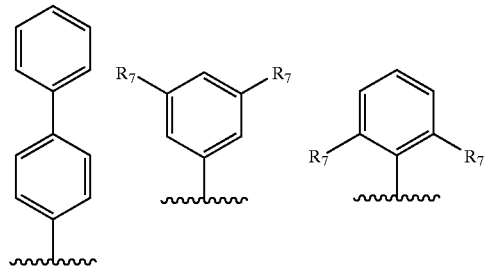

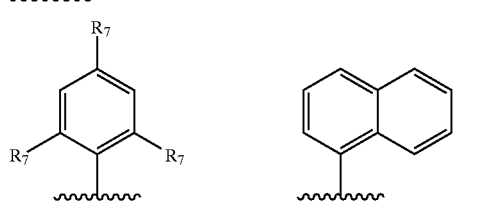

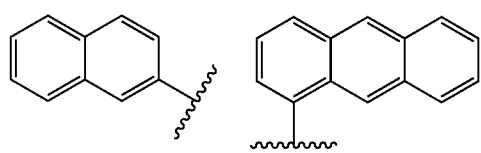

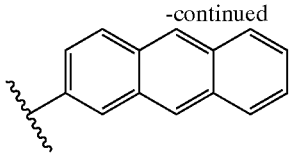

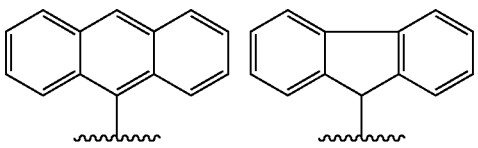

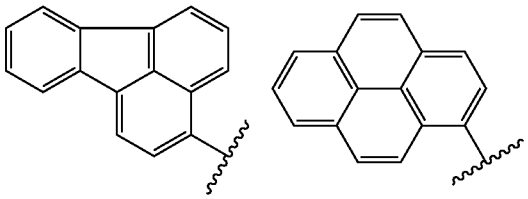

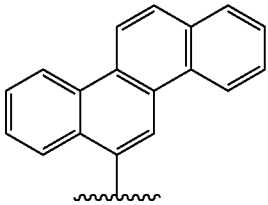

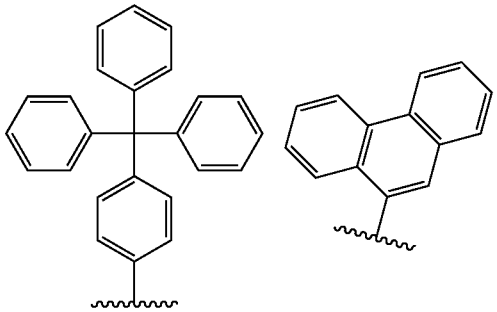

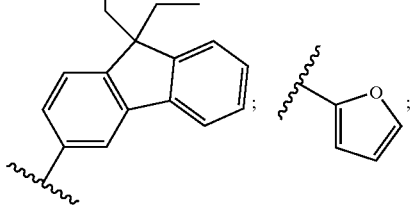

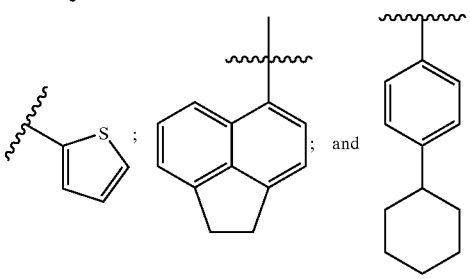

or $R_4$ and $R_5$ taken together with the nitrogen to which they are attached are selected from the group consisting of:

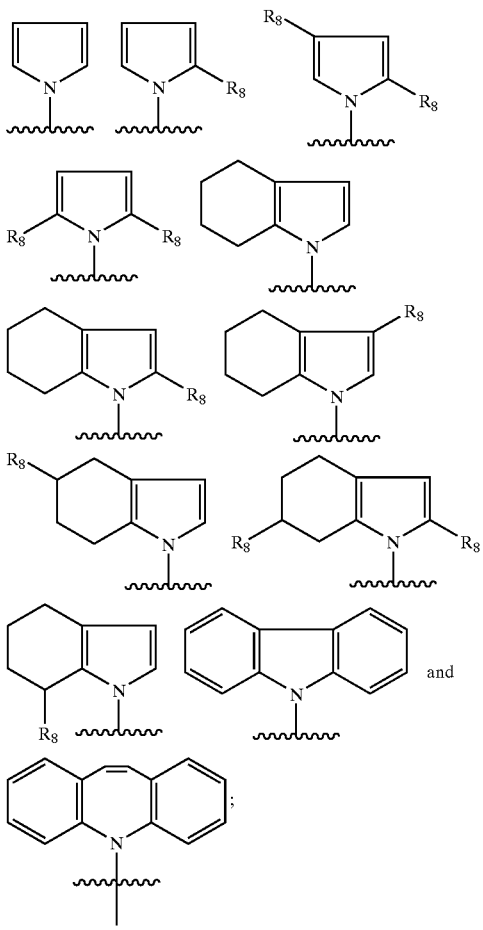

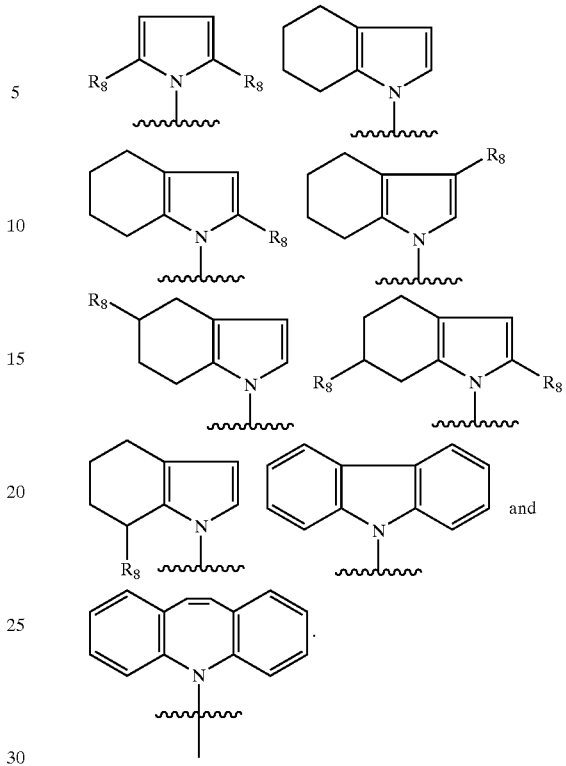

$R_6$ is $C_1$–$C_4$ straight or branched saturated alkyl;

$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and $R_9$ is selected from the group consisting of $C_1$–$C_6$ alkyl and aryl.

65. The device of claim 64, wherein $R_1$ is

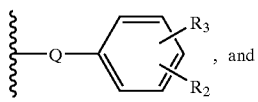, and $R_2$ and $R_3$ are each independently alkyls of 1 to 4 carbon atoms.

66. The device of claim 64, wherein $R_4$ and $R_5$ are taken together with the nitrogen to which they are attached are selected from the group consisting of:

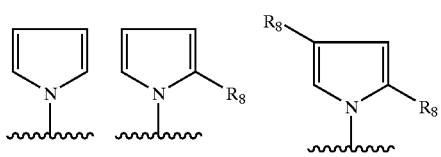

67. The device of claim 64, wherein $R_4$ and $R_5$ are taken together with the nitrogen to which they are attached and are selected from the group consisting of:

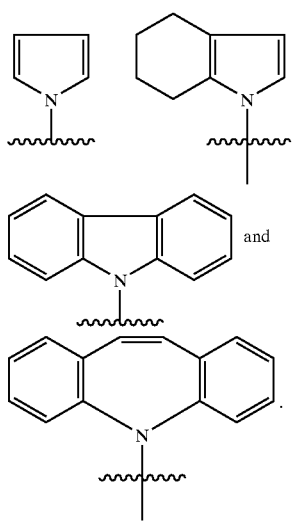

68. The device of claim 64, wherein $R_4$ and $R_5$ are each independently selected from the group consisting of phenyl, naphthyl, biphenyl, anthracenyl and fluorenyl.

69. An organic light emitting diode device comprising:
(a) a cathode;
(b) an anode; and
(c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

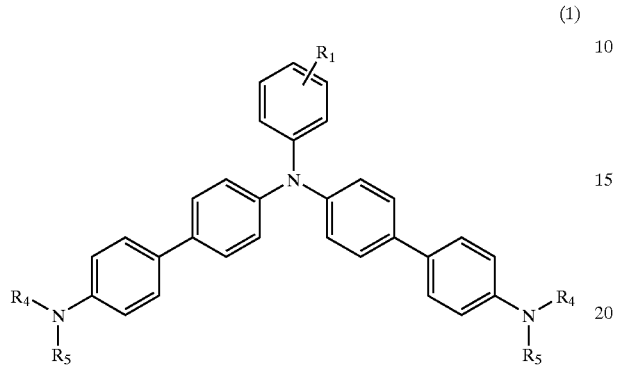
(1)

wherein $R_1$ is selected from the group consisting of biphenyl, naphthyl, phenyl and

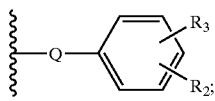

Q is a bond, $R_2$ and $R_3$ are each independently selected from the group consisting of aryl, F, Cl, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of:

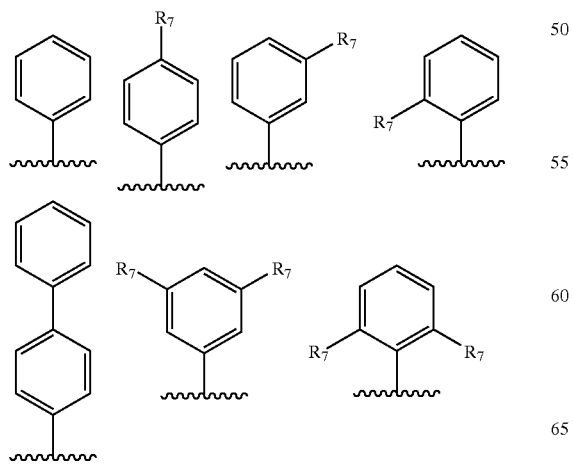

-continued

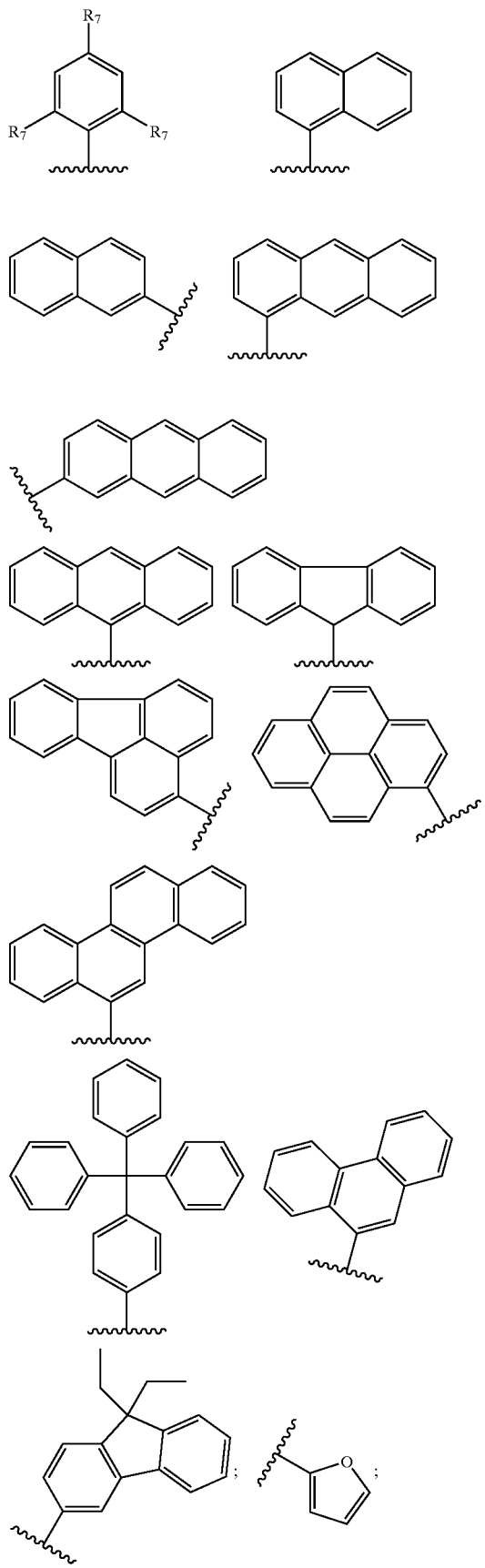

-continued

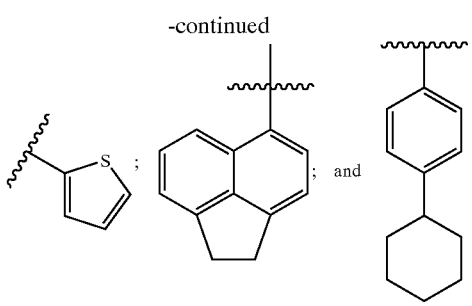

or R₄ and R₅ taken together with the nitrogen to which they are attached are selected from the group consisting of:

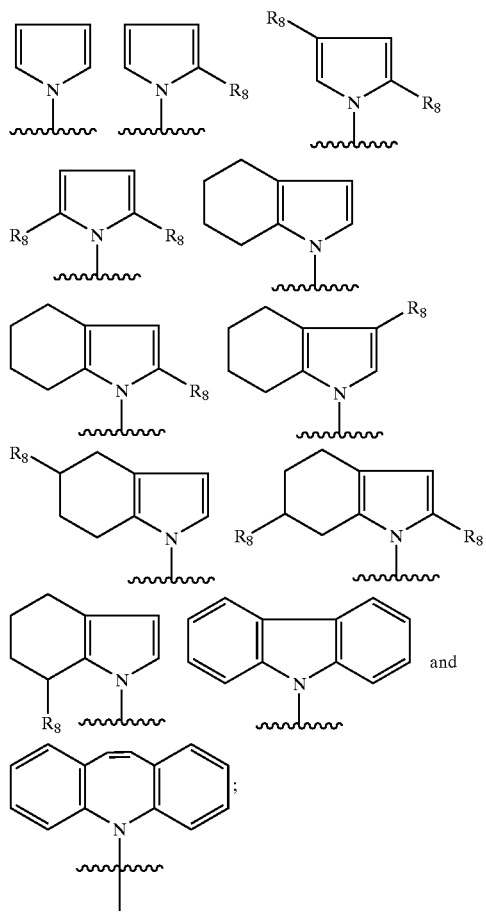

$R_6$ is $C_1$–$C_4$ straight or branched saturated alkyl;
$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and
$R_9$ is selected from the group consisting of $C_1$–$C_6$ alkyl and aryl.

70. The device of claim 71, wherein $R_1$ is

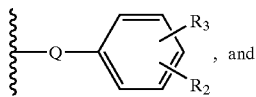 , and $R_2$ and $R_3$ are each independently alkyls of 1 to 4 carbon atoms.

71. The device of claim 69, wherein $R_2$ and $R_3$ are each aryl.

72. An organic light emitting diode device comprising:

(a) a cathode;

(b) an anode; and (c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

(1)

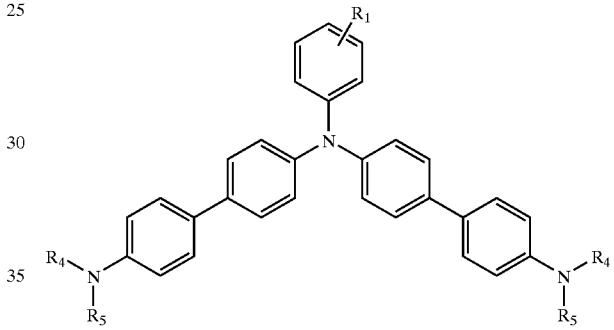

wherein $R_1$ is selected from the group consisting of biphenyl, naphthyl, phenyl and

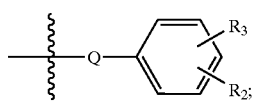

Q is selected from the group consisting of a bond, $C_1$–$C_4$ alkyl, —C(O)—, —S(O)—, —O—Si—O—, —O—Ge—O—, —O—,

and

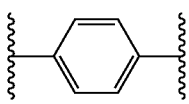

$R_2$ and $R_3$ are each aryl;
$R_4$ and $R_5$ are each independently selected from the group consisting of:

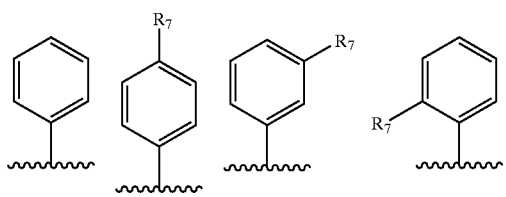
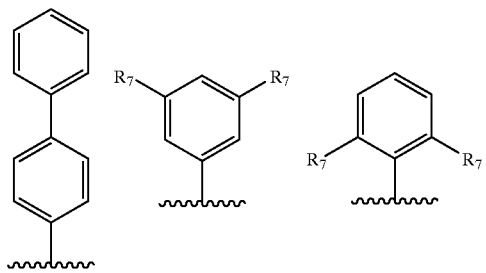
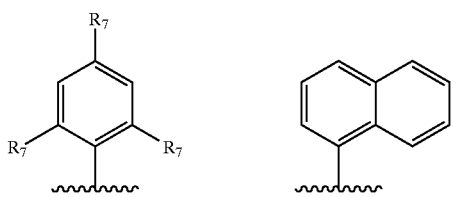
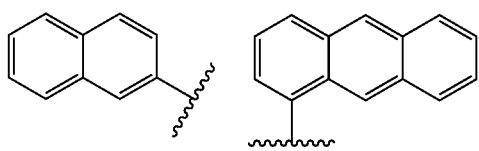
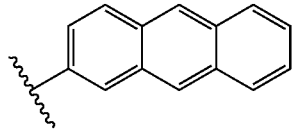
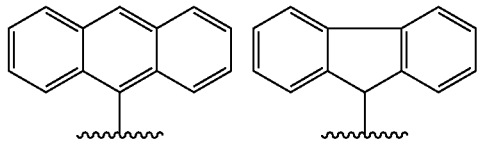
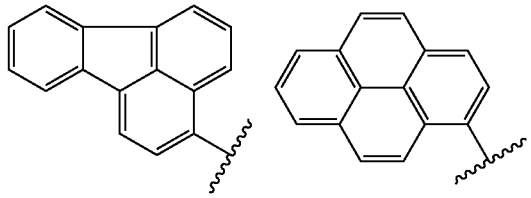
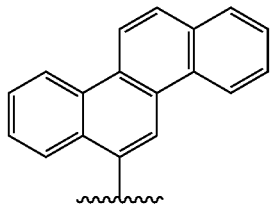
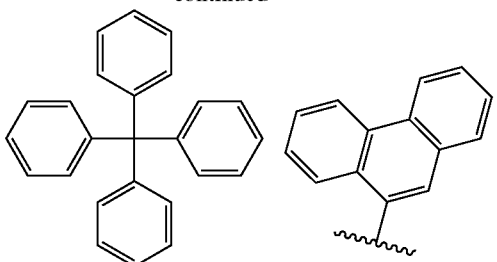
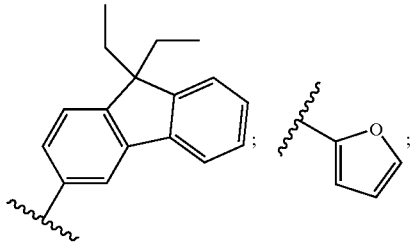
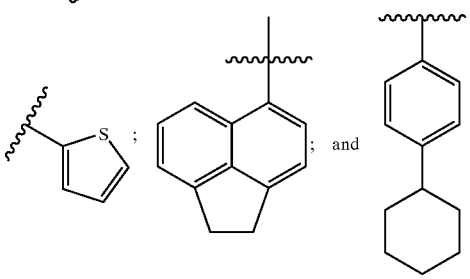
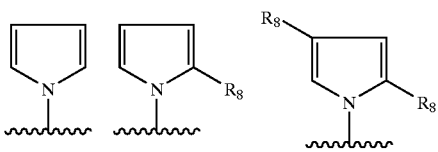
or $R_4$ and $R_5$ taken together with the nitrogen to which they are attached are selected from the group consisting of:
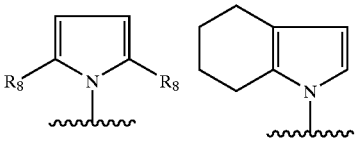
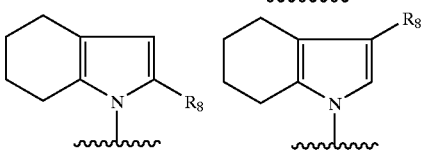
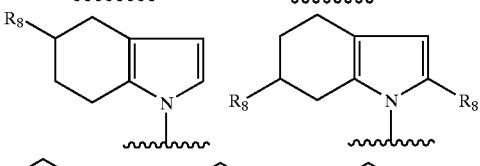
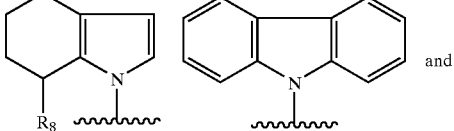
and -continued

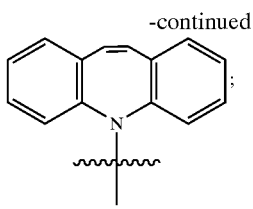

$R_6$ is $C_1$–$C_4$ straight or branched saturated alkyl, $R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and $R_9$ is selected from the group consisting of $C_1$–$C_6$ alkyl and aryl.

73. An organic light emitting diode device comprising:

(a) a cathode;

(b) an anode; and (c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

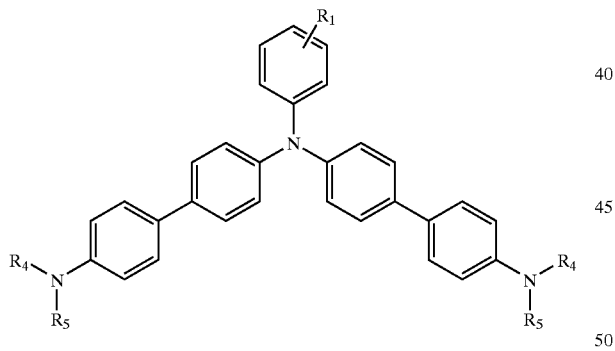

(1)

wherein $R_1$ is selected from the group consisting of biphenyl, naphthyl, phenyl and

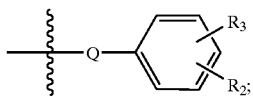

Q is selected from the group consisting of a bond, $C_1$–$C_4$ alkyl, —C(O)—, —S(O)—, —O—Si—O—, —O—Ge—O—, —O—,

and

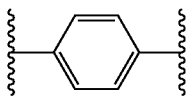

$R_2$ and $R_3$ are each $C_1$–$C_4$ straight or branched chain alkyl;

$R_4$ and $R_5$ are each independently selected from the group consisting of:

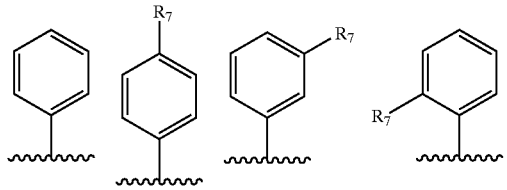

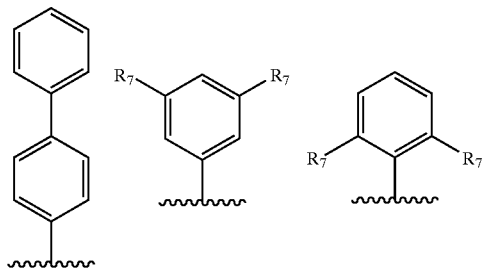

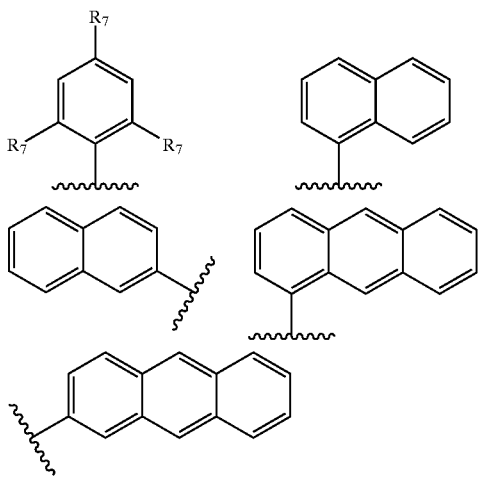

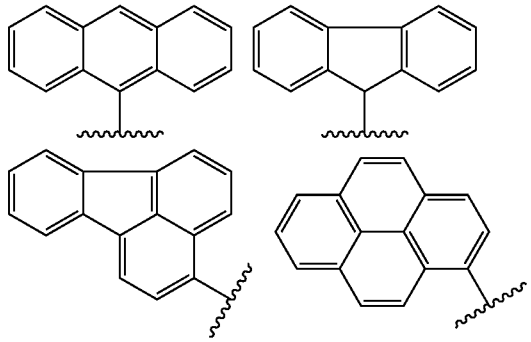

-continued

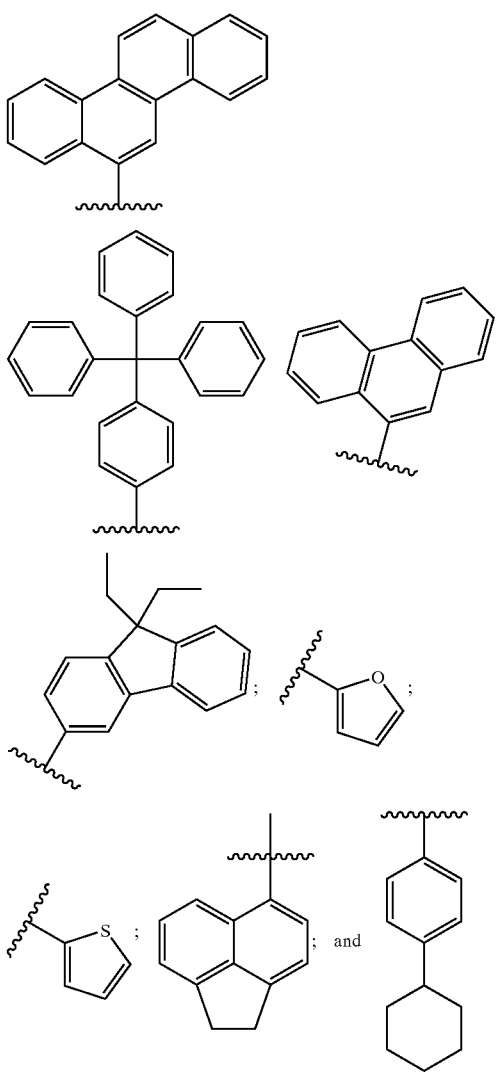

or R$_4$ and R$_5$ taken together with the nitrogen to which they are attached are selected from the group consisting of:

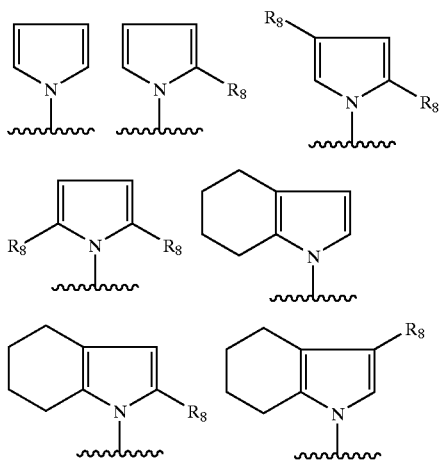

-continued

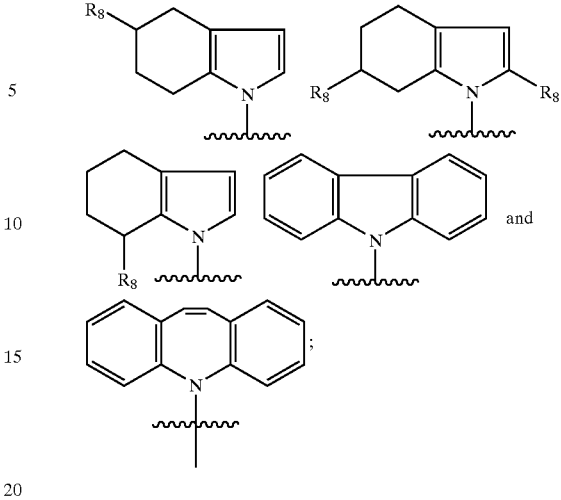

R$_6$ is C$_1$–C$_4$ straight or branched saturated alkyl;
R$_7$ and R$_8$ are each independently selected from the group consisting of —OR$_9$, C$_1$–C$_4$ alkyl, aryl, —SCH$_3$, —CF$_3$, —Cl, —Br, —NO$_2$, and —COOR$_9$; and
R$_9$ is selected from the group consisting Of C$_1$–C$_6$ alkyl and aryl.

74. An organic light emitting diode device comprising:
(a) a cathode;
(b) an anode; and
(c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

(1)

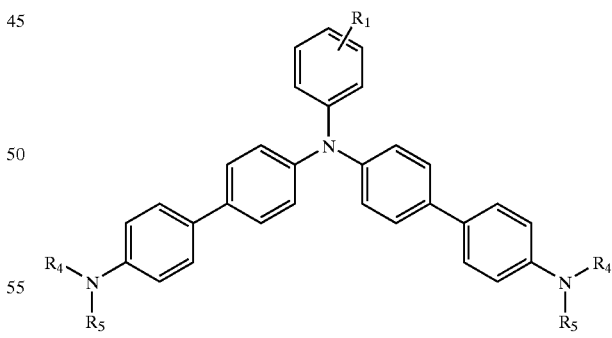

wherein R$_1$ is selected from the group consisting of biphenyl, naphthyl, phenyl and

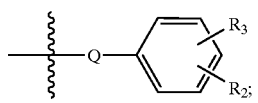

Q is selected from the group consisting of a bond, C$_1$–C$_4$ alkyl, —C(O)—, —S(O)—, —O—Si—O—, —O—Ge—O—, —O—,

and

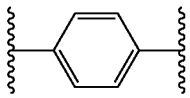

R$_2$ and R$_3$ are each independently selected from the group consisting of aryl, F, Cl, —CF$_3$, saturated alkyl of up to 10 carbon atoms, SO$_2$R$_6$, Si(R$_6$)$_3$, and OR$_6$, or R$_2$ and R$_3$ taken together form a heterocyclic ring of up to 8 atoms, wherein one of the 8 atoms is nitrogen and another of the 8 atoms is either nitrogen or oxygen, or R$_2$ and R$_3$ taken together with the phenyl group to which they are attached form a fused polycyclic aromatic system, wherein said fused polycyclic aromatic system comprises up to 16 carbon atoms;

R$_4$ and R$_5$ are taken together with the nitrogen to which they are attached form a heterocycle and are selected from the group consisting of:

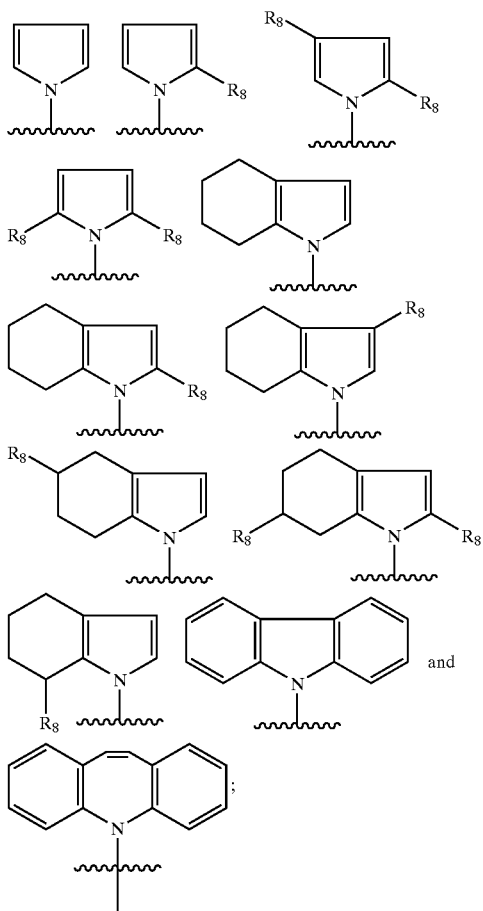

R$_6$ is C$_1$–C$_4$ straight or branched saturated alkyl;
R$_7$ and R$_8$ are each independently selected from the group consisting of —OR$_9$, C$_1$–C$_4$ alkyl, aryl, —SCH$_3$, —CF$_3$, —Cl, —Br, —NO$_2$, and —COOR$_9$; and R$_9$ is selected from the group consisting of C$_1$–C$_6$ alkyl and aryl.

75. The device of claim 74, wherein R$_1$ is

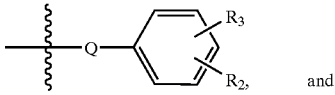

and

R$_2$ and R$_3$ are each independently alkyls of 1 to 4 carbon atoms.

76. An organic light emitting diode device comprising:
(a) a cathode;
(b) an anode; and
(c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

(1)

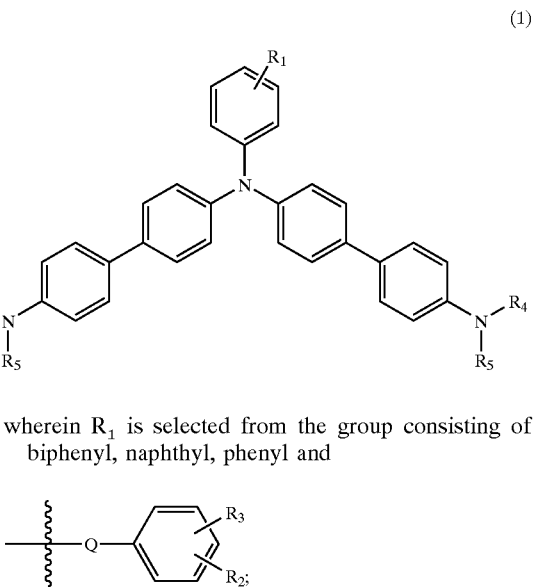

wherein R$_1$ is selected from the group consisting of biphenyl, naphthyl, phenyl and

Q is selected from the group consisting of a bond, C$_1$–C$_4$ alkyl, —C(O)—, —S(O)—, —O—Si—O—, —O—Ge—O—, —O—,

and

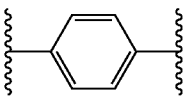

$R_2$ and $R_3$ are each independently selected from the group consisting of aryl, F, Cl, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are taken together with the nitrogen to which they are attached form a heterocycle and are selected from the group consisting of:

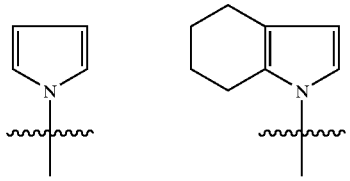

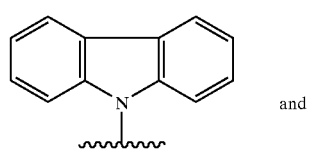 and

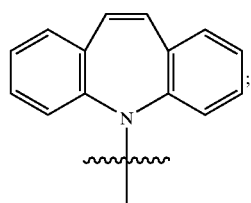

$R_6$ is $C_1$–$C_4$ straight or branched saturated alkyl;
$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and
$R_9$ is selected from the group consisting of $C_1$–$C_6$ alkyl and aryl.

77. The device of claim 76, wherein $R_1$ is

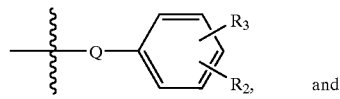 and $R_2$ and $R_3$ are independently alkyls of 1 to 4 carbon atoms.

78. An organic light emitting diode device comprising:
(a) a cathode;
(b) an anode; and
(c) at least two organic layers between said anode and said cathode, wherein said at least two organic layers comprise a first organic layer formed from at least one electron-injection/electron-transport material and a second organic layer formed from at least one hole-injection/hole-transport material, wherein said electron-injection/electron-transport material is adjacent to said cathode and said hole-injection/hole-transport material is adjacent to said anode, said at least one hole-injection/hole-transport material comprising a compound of formula 1:

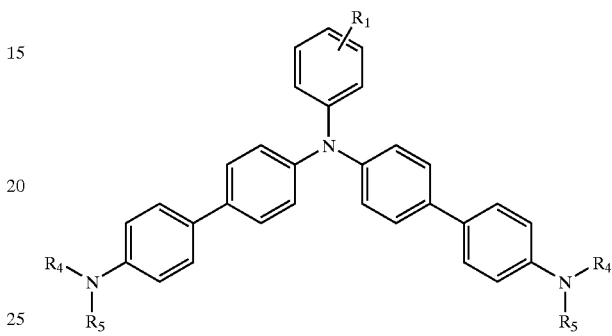

(1)

wherein $R_1$ is selected from the group consisting of biphenyl, naphthyl, phenyl and

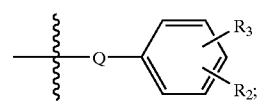

Q is selected from the group consisting of a bond, $C_1$–$C_4$ alkyl, —C(O)—, —S(O)—, —O—Si—O—, —O—Ge—O—, —O—,

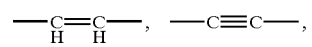

and

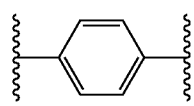

$R_2$ and $R_3$ are each independently selected from the group consisting of aryl, F, C, —$CF_3$, saturated alkyl of up to 10 carbon atoms, $SO_2R_6$, $Si(R_6)_3$, and $OR_6$, or $R_2$ and $R_3$ taken together form a heterocyclic ring of up to 8 atoms, wherein one of the 8 atoms is nitrogen and another of the 8 atoms is either nitrogen or oxygen, or $R_2$ and $R_3$ taken together with the phenyl group to which they are attached form a fused polycyclic aromatic system, wherein said fused polycyclic aromatic system comprises up to 16 carbon atoms;

$R_4$ and $R_5$ are each independently selected from the group consisting of phenyl, naphthyl, biphenyl, anthracenyl and fluorenyl;

$R_6$ is $C_1$–$C_4$ straight or branched saturated alkyl;
$R_7$ and $R_8$ are each independently selected from the group consisting of —$OR_9$, $C_1$–$C_4$ alkyl, aryl, —$SCH_3$, —$CF_3$, —Cl, —Br, —$NO_2$, and —$COOR_9$; and
$R_9$ is selected from the group consisting of $C_1$–$C_6$ alkyl and aryl.
79. The device of claim 78, wherein $R_1$ is
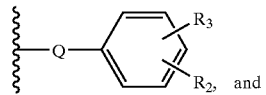 and
$R_2$ and $R_3$ are independently alkyls of 1 to 4 carbon atoms.
* * * * *